(12) United States Patent
Kamiya et al.

(10) Patent No.: US 9,842,193 B2
(45) Date of Patent: Dec. 12, 2017

(54) SWALLOWING SIMULATION APPARATUS AND METHOD

(75) Inventors: Tetsu Kamiya, Odawara (JP); Yoshio Toyama, Odawara (JP); Yukihiro Michiwaki, Musashino (JP)

(73) Assignee: MEIJI CO., LTD., Tokyo (JP)

( * ) Notice: Subject to any disclaimer, the term of this patent is extended or adjusted under 35 U.S.C. 154(b) by 982 days.

(21) Appl. No.: 14/127,420

(22) PCT Filed: Jun. 29, 2012

(86) PCT No.: PCT/JP2012/066707
§ 371 (c)(1),
(2), (4) Date: Dec. 18, 2013

(87) PCT Pub. No.: WO2013/002374
PCT Pub. Date: Jan. 3, 2013

(65) Prior Publication Data
US 2014/0120509 A1  May 1, 2014

(30) Foreign Application Priority Data
Jun. 30, 2011  (JP) .................................. 2011-146780

(51) Int. Cl.
| | | |
|---|---|---|
| *G06F 19/00* | (2011.01) | |
| *A61C 13/00* | (2006.01) | |
| *A61C 7/00* | (2006.01) | |
| *A63H 13/00* | (2006.01) | |
| *G06F 19/12* | (2011.01) | |
| *A61B 5/00* | (2006.01) | |

(52) U.S. Cl.
CPC ...... *G06F 19/3437* (2013.01); *A61C 13/0004* (2013.01); *A61B 5/4205* (2013.01); *A61C 7/002* (2013.01); *A63H 13/005* (2013.01); *G06F 19/12* (2013.01)

(58) Field of Classification Search
CPC . A61C 13/0004; A61C 7/002; G06F 19/3437; G06F 19/12; A61B 5/4205; A63H 13/005
USPC ............. 433/24; 703/11; 434/127, 267, 262, 434/263; 446/304
See application file for complete search history.

(56) References Cited

U.S. PATENT DOCUMENTS

| | | | | |
|---|---|---|---|---|
| 6,192,329 | B1 * | 2/2001 | Rider ..................... | B44C 3/042 128/922 |
| 2002/0150859 | A1 * | 10/2002 | Imgrund .................. | A61C 7/00 433/24 |
| 2010/0015589 | A1 * | 1/2010 | Lehavi ................. | G09B 23/283 434/263 |

(Continued)

OTHER PUBLICATIONS

Mizunuma et al., "Numerical Modeling and Simulation on the Swallowing of Jelly", J. of Texture Studies, vol. 40, No. 4, pp. 406-426 (2009).*

(Continued)

*Primary Examiner* — Jack Yip
(74) *Attorney, Agent, or Firm* — Squire Patton Boggs (US) LLP

(57) ABSTRACT

A swallowing simulation apparatus comprises a computer that stores swallowing simulation software that when executed results in an oral cavity model and a pseudo-food product which are analyzed in a swallowing simulation. The analysis is used to evaluate ease of eating and/or drinking.

12 Claims, 16 Drawing Sheets

CONVENTIONAL CALCULATIONAL METHOD
(LATTICE METHOD)

NEW CALCULATIONAL METHOD
(PARTICLE METHOD)

(56) References Cited

U.S. PATENT DOCUMENTS

| | | | | |
|---|---|---|---|---|
| 2011/0276159 | A1* | 11/2011 | Chun | A61C 13/0004 700/98 |
| 2012/0015316 | A1* | 1/2012 | Sachdeva | G06F 19/3437 433/24 |
| 2013/0066598 | A1* | 3/2013 | Fisker | A61C 11/00 703/1 |

OTHER PUBLICATIONS

Supplementary European Search Report for appl. No. EP 12 805238, dated Jul. 15, 2015, 9 pgs.

Bloomfield et al., "Mathematical modelling of the normal swallow", www.maths-in-medicine.org/uk/2010/swallowing/report.pdf. 10 pgs. Nov. 12, 2010.

Nicosia et al., "A planar finite element model of bolus containment in the oral cavity", Computers in Biology and Medicine vol. 37, No. 10, pp. 1472-1478 (2007).

Kobayashi et al., "Development of Swallow Robot for Research of the Mechanism for the Human Swallow", Proceeding of the 2005 JSME Conference on Robotics and Mechatronics Conference Digest, with English Abstract (2005).

Kamizu et al., The Society of Chemical Engineers $41^{st}$ Autumn Meeting Presentation Abstracts, p. 43 (2009).

Mizunuma et al., "Swallowing flow simulation for the jelly bolus", The Japan Society of Mechanical Engineers Annual Conference Proceedings, pp. 83-84 with English Abstract (2005).

Mizunuma et al.., "Ekijo Shokkai no Enge no Simulation", Dai 34 Kai Japanese Society of Biorheology Nenkai Program Shorokushu, Dai 34 Kai Japanese Society of Biorheology Nenkai Jimukyoku, SEKI, Masako, Mar. 6, 2011, p. 99.

Ishida et al., "Numerical simulation of swallowing based on videofluorography", Dai 23 Kai Bio Engineering Koen Ronbunshu, No. 10-74, The Japan Society of Mechanical Engineers, Jan. 7, 2011, pp. 559-560.

Takahiro Kikuchi et al., "Development of Swallowing Robot for Analyzing the Mechanism of Human Swallow", Dai 14 Kai Robotics Symposia Yokoshu, Robotics Symposia Un'ei linkai, Dai 14 Kai Robotics Symposia Jikko Linkai, pp. 547-552, with English Abstract Mar. 16, 2009.

International Search Report and Written Opinion for PCT/JP2012/066707, dated Oct. 2, 2012, 6 pgs.

* cited by examiner

CONVENTIONAL CALCULATIONAL METHOD
(LATTICE METHOD)

NEW CALCULATIONAL METHOD
(PARTICLE METHOD)

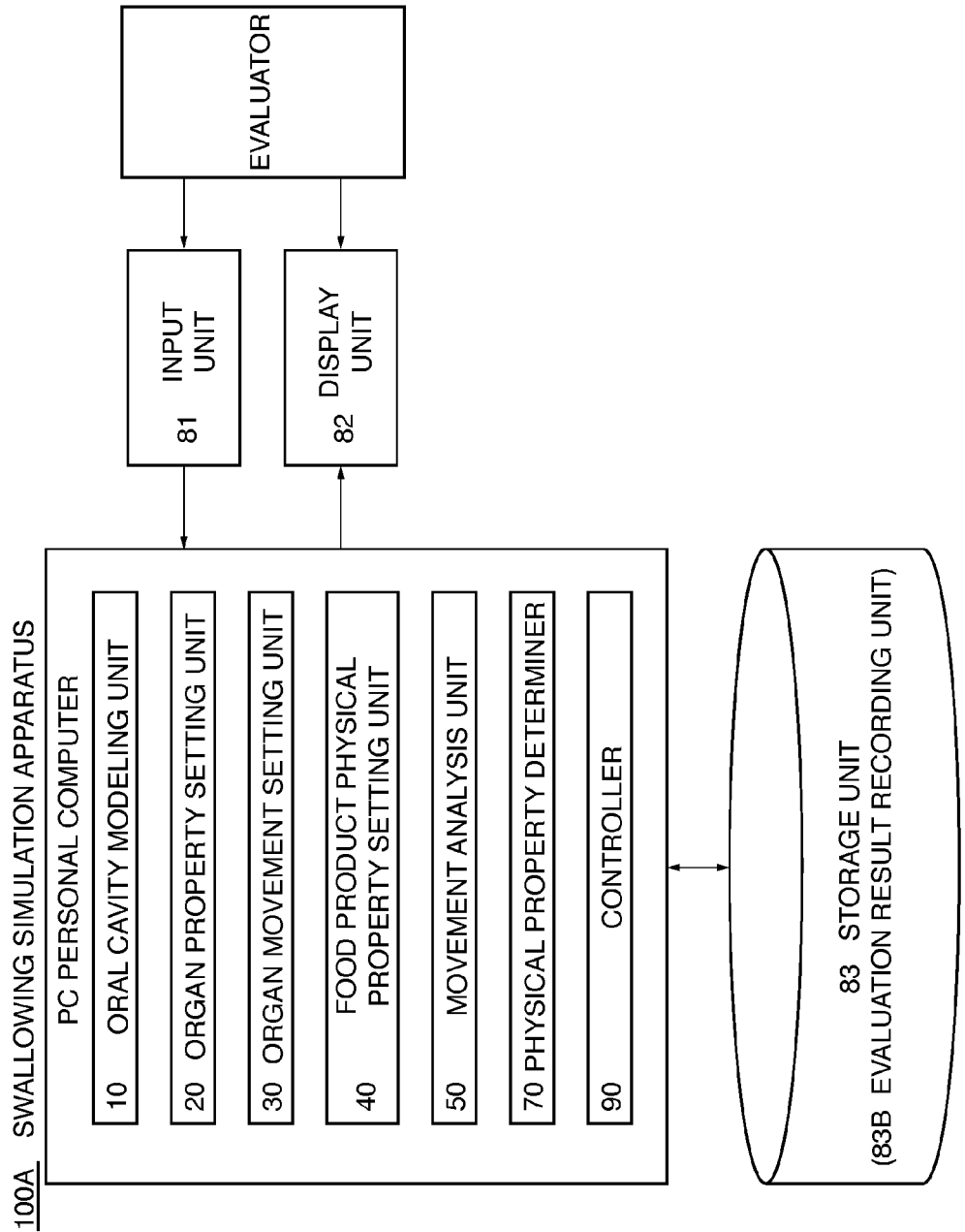

SWALLOWING SIMULATION APPARATUS AND METHOD

TECHNICAL FIELD

The present invention relates to a swallowing simulation apparatus and method. More specifically, the present invention relates to the swallowing simulation apparatus and the method that analyze behavior of a fluid and a bolus passing through an oral cavity and a throat using a particle method.

BACKGROUND ART

The swallowing action, in particular, the physical property of the food product and the movements of the oral cavity organs during swallowing, is complicated. Therefore, it is extremely difficult to grasp the phenomenon itself accurately. However, in the fields of medical treatment and nursing, to prevent accidental swallowing and accidental ingestion by an old person and a handicapped person, reductions in risks of accidental swallowing and accidental ingestion have been strived through repetition of various trials and errors. Given that recently there have been accident of choking on konjac jelly, in general food products, it is required to assure safety of a food product using an objective value and index.

Two methods are available for solution of the swallowing phenomenon: a method that directly obtains biological information such as a videofluoroscopic swallowing or a myoelectric potential measurement and a method that indirectly obtains information using, for example, a swallowing robot or a numerical value simulation.

FIG. 13 illustrates exemplary videofluoroscopic swallowing (images taken by X-ray). In the left diagram, liquid 49 is in an oral cavity. In the middle diagram, the liquid 49 partially flows to a throat. In the right diagram, the liquid 49 has been swallowed and disappeared.

FIG. 14 illustrates an exemplary myoelectric potential measurement. Electrodes are attached to a masseter and a suprahyoid muscle group to measure a myoelectric potential waveform. Then, the myoelectric potential waveform is integrated to calculate a muscle activity amount.

Although the method that directly obtains biological information allows grasping a behavior during swallowing accurately, in gathering data under various conditions, there is a disadvantage that a considerable load is taken to an examinee.

Meanwhile, one method of indirectly obtaining the information is to use the swallowing robot (see Non-Patent Literature 1). The swallowing robot is very useful for understanding of simple principle of the swallowing phenomenon. However, a behavior and a structure of each of the oral cavity organs of the robot is not easily changed.

Up to the present, numerical analyses on a behavior of a fluid or a bolus such as a solid material in a living body have been performed. For the fluid, an inside of an analysis target region is separated by a grid referred to as a mesh. Calculations have been performed using a lattice method that analyzes physical quantities (speed, temperature, pressure) at the grid point and the inside of the grid (see Non-Patent Literature 2). In the case of treating the bolus as a semisolid, calculations have been performed using a structural analysis method for machine components such as a finite element method (see Non-Patent Literature 3).

PRIOR ART DOCUMENT

Non-Patent Literature

Non-Patent Literature 1: Kobayashi, et al., Conference on Robotics and Mechatronics Conference Digest, 2005, 117

Non-Patent Literature 2: Kamizu, et al., The Society of Chemical Engineers 41st Autumn Meeting Presentation Abstracts, 2009, P 09

Non-Patent Literature 3: Mizunuma, et al., The Japan Society of Mechanical Engineers Annual Conference Proceedings, 2005(2), 83-84

DISCLOSURE OF INVENTION

Problem to be Solved by the Invention

However, with the lattice method, which is a mainstream of the conventional numerical analysis, phenomena such as a large deformation of a surface and a spraying seen at the fluid or the bolus while actually being swallowed are difficult to be caught. Accordingly, reproduction of the actual phenomenon has been difficult.

An object of the present invention is to provide a swallowing simulation apparatus and a swallowing simulation method that facilitate approximate reproduction of an actual phenomenon of swallowing.

Means for Solving the Problem

To solve the above described problems, a swallowing simulation apparatus 100A according to the first aspect of the present invention comprises, as shown in, for example, FIG. 2; an oral cavity modeling unit 10 configured to form an oral cavity model 11 (see FIG. 3) formed of oral cavity organs; an organ property setting unit 20 configured to set an organ property of each of the oral cavity organs in the oral cavity model 11; an organ movement setting unit 30 configured to set a movement of each of the oral cavity organs in the oral cavity model 11; a food product physical property setting unit 40 configured to set a food product, a medicinal product or a nonmedicinal product (hereinafter referred to as food product or similar product) as an analysis target, and a physical property of the food product or similar product; an input unit 81 configured to input a pseudo food product to the oral cavity, the pseudo food product being formed by modeling the food product or similar product; a movement analysis unit 50 configured to analyze a movement of each of the oral cavity organs and a behavior of the pseudo food product 41 (see FIG. 4) while being swallowed in the oral cavity model 11 using a particle method; and a display unit 82 configured to display an analysis result of the movement of each of the oral cavity organs and the behavior of the pseudo food product 41 while being swallowed on a moving screen, the analysis result being analyzed by the movement analysis unit 50.

Here, the oral cavity organs are constituted by, an oral cavity wall 12, a gullet 13, a respiratory tract 14, a tongue 15, a soft palate 16, an epiglottis 17 and the like (see FIG. 3). The oral cavity wall 12 is constituted of a hard palate (front side) and the soft palate 16 (back side). The soft palate 16 is a soft mucous membrane portion at a rearward of the hard palate. The soft palate 16 includes a palatine velum and a uvula. The palatine velum cuts off a nasal cavity and an oral cavity during swallowing. The uvula is a portion hung down from the palatine velum. The oral cavity model 11 is constituted including each of the oral cavity organs. The gullet 13 and the respiratory tract 14 only need to include an entrance portion. The oral cavity model 11 is preferred to be formed according to the actual movements of the oral cavity organs. However, a movable part of the oral cavity model 11 may be limited for simplifying and facilitating the analysis. The organ properties of each of the oral cavity organs include, its dimensions, whether it is an elastic body or a rigid body, and if it is an elastic body, the elastic modulus, and related properties. The movements of each of the oral cavity organs include a movement, a rotation, a periodic movement and the like. When a food product is liquid, a physical property of the food product includes a fluid volume, a degree of viscosity, a surface tension, and a specific gravity. When the food product is a semisolid (with plasticity but without fluidity), the physical property includes an amount, a degree of viscosity, a specific gravity, a yield point, yield point stress, shear rate dependence of degree of viscosity, dynamic viscoelasticity, static viscoelasticity, compressive stress, adhesiveness, and cohesiveness. When the food product is a solid, the physical property includes a shape, dimensions, an elastic modulus, tensile strength, a yield point, yield point stress, shear rate dependence of degree of viscosity, dynamic viscoelasticity, static viscoelasticity, compressive stress, breaking stress, breaking strain, hardness, adhesiveness, cohesiveness and the like. A behavior of a pseudo food product while being swallowed is typically referred to as a behavior of movement from an oral cavity to a gullet through a throat. However, the behavior also includes cases where the pseudo food product returns to the oral cavity without reaching the throat or the gullet and cases where the pseudo food product enters the respiratory tract or the nasal cavity.

An input unit 81, for example, includes a computer mouse and a keyboard. Dragging the computer mouse to an inside of the oral cavity of the oral cavity model 11 inputs the pseudo food product (includes a pseudo medicinal product or a pseudo nonmedicinal product). Or, a food product input setting unit 45 (see FIG. 11) may be disposed and the pseudo food product and an injection position and injection time of the pseudo food product may be preset so as to automatically inject the pseudo food product. A movement analysis unit 50 analyzes using a particle method. Moving particle-Semi-implicit (an MSP) method, for example, is applicable. As for "display on a moving screen" relating to a display unit 82, a display on the moving screen such as a liquid crystal display is typically used. Displaying the moving screen is useful for an evaluator to observe the moving screen for evaluation. However, for automatic evaluation, a pseudo screen display unit 82A (see FIG. 11) is disposed in a computer and an evaluation condition storage unit 83A (see FIG. 11) is disposed in a storage unit 83. Analysis results are dynamically displayed on a virtual moving screen of the pseudo screen display unit 82A. Then, the analysis results are collated with the evaluation condition stored in the evaluation condition storage unit 83A, and evaluated in an evaluation unit 60 (see FIG. 11) in the computer. However, the "display on a moving screen" also includes the case where the analysis results are thus dynamically displayed on the virtual moving screen of the pseudo screen display unit 82A. The display unit 82 includes the pseudo screen display unit 82A.

With the configuration according to this aspect, the organ properties, the movements of the oral cavity organs, and the physical property of the food product are set in the oral cavity model 11. Then, the behavior of the food product is analyzed using the particle method. This allows providing the swallowing simulation apparatus that facilitates approximate reproduction of the actual phenomenon of swallowing.

The swallowing simulation apparatus of the second aspect is that according to the first aspect of the present invention, as shown in, for example, FIG. 3 (for a configuration of the swallowing simulation apparatus, see FIG. 2, the same applies to the following); wherein the organ property setting unit 20 sets an oral cavity wall 12 as a rigid body and a tongue 15 as an elastic body; the organ movement setting unit 30 sets a plurality of moving walls 18 in the tongue 15, the tongue 15 being set so as to move in a peristaltic movement or a wave movement by moving the plurality of moving walls 18 to a direction intersecting with a surface of the tongue 15 with a predetermined period and a predetermined phase difference, and sets a soft palate 16, an epiglottis 17, and a gullet wall 19 so as to move together with a predetermined phase difference to the peristaltic movement or the wave movement; and the movement analysis unit 50 treats the tongue 15 and the pseudo food product 41 as particles.

Here, the surface of the tongue 15 is referred to as a surface of a near side (upper side). The peristaltic movement is referred to as a simulated movement of a movement of a digestive system such as a large bowel, a small bowel or the like. Meanwhile, a wave movement is referred to as a simulated movement of a movement of wave.

With the configuration according to this aspect, setting movements of a plurality of moving walls 18 to the same period and a shifting phase allows a peristaltic movement or the wave movement of the tongue to be reproduced close to the actual phenomenon. This allows approximate reproduction of the actual phenomenon in the swallowing phenomenon.

The swallowing simulation apparatus of the third aspect of the present invention is that according to the second aspect, as shown in, for example, FIG. 3; wherein the organ movement setting unit 20 sets a movement of each of a soft palate 16 and an epiglottis 17 as a movement of a rotator where a rotational center moves.

With the configuration according to this aspect, movements of the soft palate 16 and the epiglottis 17 can be reproduced close to the actual phenomena.

The swallowing simulation apparatus of the fourth aspect of the present invention is that according to any one of the first aspect to the third aspect, as shown in, for example, FIG. 6; wherein the food product physical property setting unit 40 sets a plurality of liquid, semisolid, or solid pseudo food products 42, 43 with different physical property as an analysis target; and the movement analysis unit 50 determines free surfaces of a plurality of the pseudo food products 42, 43 and boundaries between the plurality of pseudo food products 42, 43, the movement analysis unit 50 analyzing a gearing behavior of the plurality of pseudo food products 42, 43.

With the configuration according to this aspect, the gearing behavior of the plurality of pseudo food products can be reproduced close to the actual phenomenon, effective in analysis of the gearing behavior.

The swallowing simulation apparatus of the fifth aspect of the present invention is that according to any one of the first aspect to the fourth aspect, as shown in, for example, FIG. 11, the apparatus further comprises; an evaluation unit 60 configured to evaluate easiness of eating and/or easiness of drinking of the food product or similar product based on the behavior of the pseudo food product 41 while being swallowed on the moving screen; wherein, the moving screen is a virtual moving screen formed at a virtual space by the swallowing simulation apparatus 100B to simulatively display an analysis result of a movement of each of the oral cavity organs and a behavior of the pseudo food product 41 to 44 while being swallowed, the analysis result being analyzed by the movement analysis unit 50; and the evaluation unit 60 evaluates whether the behavior of the pseudo food product on the virtual moving screen meets a predetermined condition or not.

Here, the virtual moving screen is referred to as a virtual moving screen formed at a virtual space on a personal computer PC. However, the virtual moving screen displays the same contents as contents of the moving screen when displayed on the display unit 82. For automatic evaluation, the pseudo screen display unit 82A is disposed in the computer and the evaluation condition storage unit 83A is disposed in the storage unit 83. Analysis results are dynamically displayed on the virtual moving screen of the pseudo screen display unit 82A. Then, the analysis results are collated with the evaluation condition stored in the evaluation condition storage unit 83A for evaluation. The "display on a moving screen" also includes the case where the analysis results are thus dynamically displayed on the virtual moving screen. Predetermined conditions include, for example, the following. A food product does not enter the respiratory tract, not get blocked in the gullet, not adhere to the tongue or the gullet, a period from introduction in the oral cavity to passing through the gullet is within a predetermined range, stress applied to a wall surface is equal to or less than a predetermined value, shear stress at the wall surface is equal to or less than a predetermined value or the like.

With the configuration according to this aspect, the analysis result displayed on the virtual moving screen and the evaluation condition stored in the evaluation condition storage unit 83A are collated. Thus, easiness of eating and/or easiness of drinking of the food product or similar product can be automatically evaluated.

The swallowing simulation apparatus of the sixth aspect of the present invention is that according to any one of the first to the fifth aspects, as shown in, for example, FIG. 3 (for a configuration of the apparatus, see FIG. 2); wherein the oral cavity modeling unit 10 forms a two dimensional oral cavity model 11; and the movement analysis unit 50 analyzes the behavior of the pseudo food product 41 in a two dimensional space.

With the configuration according to this aspect, the behavior of the pseudo food product 41 under the swallowing simulation is approximately expressed in a two dimensional space. This allows efficiently evaluating easiness of eating and/or easiness of drinking of the food product based on a simple analysis.

The swallowing simulation apparatus according of the seventh aspect of the present invention further comprises, as shown in, for example, FIG. 2; an evaluation result recording unit 83B configured to record an evaluation result of easiness of eating and/or easiness of drinking of the food product or similar product based on an analysis result of the behavior of the pseudo food product 41 while being swallowed; and a physical property determiner 70 configured to determine the physical property of the food product or similar product regarded as appropriate based on the evaluation result recorded in the evaluation result recording unit 83B.

Here, the swallowing simulation apparatus 100A automatically determines the physical property based on the evaluation result. An aspect of determination by a human (for example, an evaluator) is also possible. However, a physical property determiner may be absent here. The physical property determiner is not used even if provided, or the determination result is provided to the evaluator as a reference.

With the configuration according to this aspect, a physical property of the food product or similar product with appropriate easiness of eating and/or easiness of drinking of the food product or similar product can be efficiently derived through the simulation that facilitates the approximate reproduction of the actual phenomenon of swallowing.

The swallowing simulation method according to the eighth aspect of the present invention comprises, as shown in, for example, FIG. 10 (for a configuration of the apparatus, see FIG. 2); an oral cavity modeling step (S010) of forming an oral cavity model 11 formed of oral cavity organs; an organ property setting step (S020) of setting an organ property of each of the oral cavity organs in the oral cavity model 11; an organ movement setting step (S030) of setting a movement of each of the oral cavity organs in the oral cavity model 11; a food product physical property setting step (S040) of setting a food product or similar product as an analysis target and a physical property of the food product or similar product; an input step (S050) of inputting a pseudo food product 41 to the oral cavity, the pseudo food product being formed by modeling the food product or similar product; a movement analysis step (S060) of analyzing a movement of each of the oral cavity organs and a behavior of the pseudo food product 41 while being swallowed in the oral cavity model using a particle method; and a display step (S070) of displaying an analysis result of the movement of each of the oral cavity organs and the behavior of the pseudo food product 41 while being swallowed on a moving screen, the analysis result being analyzed in the movement analysis step (S060).

With the configuration according to this aspect, the organ properties, the movements of the oral cavity organs, and the physical property of the food product in the oral cavity model 11 are set. Then, the behavior of the food product is analyzed using the particle method. This allows providing the swallowing simulation method that facilitates the approximate reproduction of the actual phenomenon of swallowing.

The swallowing simulation method according to the ninth aspect of the present invention comprises, as shown in, for example, FIG. 10; an evaluation step (S080) of evaluating easiness of eating and/or easiness of drinking of the food product or similar product based on an analysis result of the behavior of the pseudo food product 41 while being swallowed; and a physical property determination step (S090) of determining a physical property of the food product or similar product regarded as appropriate based on an evaluation result evaluated in the evaluation step (S080).

With the configuration according to this aspect, the physical property of the food product or similar product with appropriate easiness of eating and/or easiness of drinking of the food product or similar product can be efficiently derived through the simulation that facilitates the approximate reproduction of the actual phenomenon of swallowing.

A computer readable program according to a tenth aspect of the present invention makes the computer execute the swallowing simulation method according to the eighth or the ninth aspect.

Here, the program may be stored in a storage unit built into the computer. The program may be downloaded from the Internet. The program may be stored in a memory medium readable by the computer. The computer according to the aspect includes a computer of an apparatus configured including the computer (for example, the personal computer PC) like the swallowing simulation apparatus.

To solve the above described problems, a swallowing simulation apparatus 400A according to the eleventh aspect of the present invention comprises, as shown in, for example, FIG. 15; an oral cavity modeling unit 10 configured to form an oral cavity model 11 (see FIG. 3) formed of oral cavity organs; an organ movement setting unit 30 configured to set a movement of each of the oral cavity organs in the oral cavity model 11; a food product physical property setting unit 40 configured to set a food product or similar product as an analysis target and a physical property of the food product or similar product; an input unit 81 configured to input a pseudo food product 41 to the oral cavity, the pseudo food product being formed by modeling the food product or similar product; a movement analysis unit 50 configured to analyze a movement of each of the oral cavity organs and a behavior of the pseudo food product 41 (see FIG. 4) while being swallowed in the oral cavity model 11 using a particle method; a display unit 82 configured to display an analysis result of the movement of each of the oral cavity organs and the behavior of the pseudo food product 41 while being swallowed on a moving screen, the analysis result being analyzed by the movement analysis unit 50; and an organ movement determiner 75 configured to determine an organ movement parameter fitting to a behavior or a symptom of an organ of diagnosed person based on the analysis result analyzed in the movement analysis unit 50 in the organ movement parameters set in the organ movement setting unit 30.

With this configuration, since the behavior of the organ is analyzed using the particle method, an evaluation close to the actual phenomenon on exercise capacity of the organ of a diagnosed person can be performed.

The diagnosis assistance apparatus according to a twelfth aspect of the present invention comprises the swallowing simulation apparatus 100C of the eleventh aspect; the swallowing simulation apparatus including an evaluation result recording unit 83B configured to record an evaluation result of easiness of eating and/or easiness of drinking of the food product or similar product based on an analysis result of a behavior of the pseudo food product 41 while being swallowed; a medical treatment diagnosis result database that records a diagnosis result on a patient or a person subject to checkup; and a diagnosis result comparator configured to compare a diagnosis result recorded in the medical treatment diagnosis result database with an evaluation result recorded in the evaluation result recording unit.

With the configuration according to this aspect, since the behavior of the organ is analyzed using the particle method, a diagnosis assistance apparatus that allows evaluation close to the actual phenomenon on exercise capacity of the organ of the diagnosed person can be provided.

A swallowing simulation method according to a thirteenth aspect of the present invention comprises, as shown in, for example, FIG. 16; an oral cavity modeling step (S010) of forming an oral cavity model 11 formed of oral cavity organs; an organ movement setting step (S030) of setting a movement of each of the oral cavity organs in the oral cavity model 11; a food product physical property setting step (S040) of setting a food product or similar product as an analysis target and a physical property of the food product or similar product; an input step (S050) of inputting a pseudo food product 41 into the oral cavity, the pseudo food product 41 being formed by modeling the food product or similar product; a movement analysis step (S060) of analyzing a movement of each of the oral cavity organs and a behavior of the pseudo food product 41 while being swallowed in the oral cavity model 11 using a particle method; a display step (S070) of displaying an analysis result of the movement of each of the oral cavity organs and the behavior of the pseudo food product 41 while being swallowed on a moving screen, the analysis result being analyzed in the movement analysis step (S060); and an organ movement determination step (S096) of determining an organ movement parameter fitting a behavior or a symptom of an organ of diagnosed person based on the analysis result analyzed in the movement analysis step (S060) in the organ movement parameters set in the organ movement setting step (S030).

With the configuration according to this aspect, since the behavior of the organ is analyzed using the particle method, a diagnosis assistance apparatus that allows evaluation close to the actual phenomenon on exercise capacity of the organ of the diagnosed person can be provided.

Effect of the Invention

According to the present invention, a swallowing simulation apparatus and a swallowing simulation method that facilitate reproduction of an actual phenomenon of swallowing can be provided.

BRIEF DESCRIPTION OF DRAWINGS

FIG. 2 illustrates an exemplary configuration of a swallowing simulation apparatus according to a first embodiment.

BEST MODE FOR CARRYING OUT THE INVENTION

The present application is based on Japanese Patent Application No. 2011-146780 filed on Jun. 30, 2011 in Japan. The content forms part thereof as the content of the present application. The present invention will be more completely understood by the detailed description provided hereinafter. Further areas of applicability of the invention will become more apparent from the detailed description provided hereinafter. However, it should be understood that the detailed description and specific examples indicate desired embodiments of the invention, and are provided for the purpose of illustration only because it will be apparent to those skilled in the art that various modifications and variations can be made without departing from the spirit or scope of the present invention from the detailed description. Applicants have no intention to present any described embodiments to the public, and among modifications and variations, the subject matter that may not be fallen within the scope of claims should also be part of the invention under the doctrine of equivalents.

Embodiments of the present invention will be described hereinafter in detail with reference to the drawings. In each drawing, like numerals and symbols will be used for identical or like elements, and duplicate descriptions may not be repeated.

(Particle Method)

According to the embodiment, as an analysis method that allows expressing a large deformation of a liquid surface, a spray and the like, the particle method that treats liquid and solid analysis targets as particles is employed for simulations. First, the particle method will be described.

Figure 1A:
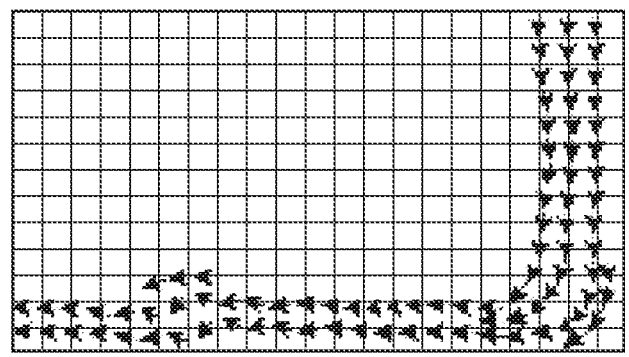
FIG. 1A describes a lattice method (conventional analysis method).
Figure 1B:
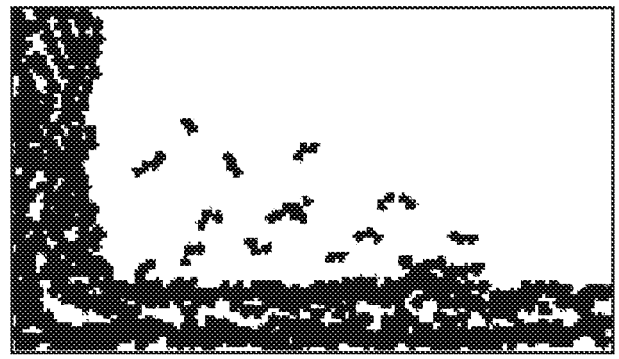
FIG. 1B describes a particle method (new analysis method)

FIG. 1A and FIG. 1B illustrate a difference between a lattice method, which is the conventional analysis method, and the particle method, which is a new analysis method. FIG. 1A illustrates a conceptual diagram of the lattice method while FIG. 1B illustrates a conceptual diagram of the particle method. The lattice method divides an analysis region by grid and calculates physical quantities of each grid. That is, a change in the liquid surface goes along a shape of the grid. Accordingly, an analysis of a case when the spray occurs or the liquid surface is largely deformed is difficult. In contrast to this, the particle method, especially an Moving particle-Semi-implicit (MPS) method is comparatively new analysis method, which was developed in 1995 (Koshizuka et al, Comput. Fluid Dynamics J, 4, 29-46, 1995). The particle method replaces a fluid with particles and calculates the physical quantities of each particle. As a result, a subtle change in the liquid surface can be analyzed, allowing an analysis when the spray occurs or the liquid surface is largely deformed. However, fluids and boluses in vivo have not been analyzed using the particle method up to the present. Therefore, the inventors have developed the simulation apparatus and the simulation method where the particle method is applied to estimation of behaviors of the liquid or the bolus in the living body. The following describes the embodiments.

In the MPS method, as a governing equation for an incompressible flow, a conservation-of-mass formula and a conservation-of-momentum formula are established. Lagrangian derivative may be used for the time derivative in the conservation-of-momentum formula. Terms expressing movement and flow need not be denoted explicitly. A weighting function $w(r)$ (a function of a distance r between particles, and expressed by $w(r)=r_E/r-1$; $0 \leq r < r_E$, and $w(r)=0$; $r_E < r$, being a decreasing function of the distance r between particles within a constant separation $r_E$, being 0 with outside the constant distance $r_E$) is introduced, and the weighting function is used for particle interaction. A Laplacian model is established on the physical quantities in the positions of each particle in the particle interaction model, and the discretization equations are solved. Solving this discretization equation in accordance with a solution method of a matrix equation, a speed is obtained. Then the position of each particle is determined.

A simulator (analysis software) to perform the swallowing simulation method according to the embodiment models the oral cavity organs and analyzes the behaviors of the fluid or the bolus while passing through the oral cavity and the throat using the particle method.

From the analysis results using the simulator, for example, the following are performed.

(a) An estimation of risk of a swallowing an accidental swallowing or an accidental ingestion depending on the difference in a physical property value of a food product or similar product (b) An estimation of a swallowing period depending on the difference in the physical property value of the food product or similar product (c) Estimations of a force and shear stress applied to the throat wall depending on the difference in the physical property value of the food product or similar product (d) Evaluations on easiness of drinking, easiness of eating, difficulty of drinking, and difficulty of eating based on the correlations between the above described data and a sensory evaluation.

The evaluations are made by the evaluator or automatically made by the swallowing simulation apparatus.

First Embodiment (Swallowing Simulation Apparatus Configuration)

FIG. 2 illustrates an exemplary configuration of the swallowing simulation apparatus 100A according to the first embodiment. The first embodiment describes an exemplary swallowing evaluation made by the evaluator's inputting the food product and viewing the moving image.

The swallowing simulation apparatus 100A includes an oral cavity modeling unit 10, an organ property setting unit 20, an organ movement setting unit 30, a food product physical property setting unit 40, an input unit 81, a movement analysis unit 50, a display unit 82, a physical property determiner 70, a controller 90, and a storage unit 83. The oral cavity modeling unit 10 forms an oral cavity model formed of oral cavity organs. The organ property setting unit 20 sets an organ property of each of the oral cavity organs in the oral cavity model. The organ movement setting unit 30 sets a movement of each of the oral cavity organs in the oral cavity model. The food product physical property setting unit 40 sets a food product as an analysis target and a physical property of the food product. The input unit 81 inputs a pseudo food product, which is formed by modeling the food product, to the oral cavity. The movement analysis unit 50 analyzes a movement of each of the oral cavity organs and a behavior of the pseudo food product while being swallowed in the oral cavity model using a particle method. The display unit 82 displays analysis results of the movement of each of the oral cavity organs and the behavior of the pseudo food product while being swallowed analyzed by the movement analysis unit 50 on a moving screen. The physical property determiner 70 determines a physical property of a food product or similar product regarded as appropriate based on the evaluation result. The controller 90 controls the swallowing simulation apparatus 100A and each unit of the swallowing simulation apparatus 100A to have functions required for the swallowing simulation apparatus 100A. The storage unit 83 stores the oral cavity model, the organ properties, the setting conditions, the analysis results, and the evaluation results. Among these units, the oral cavity modeling unit 10, the organ property setting unit 20, the organ movement setting unit 30, the food product physical property setting unit 40, the movement analysis unit 50, the physical property determiner 70, and the controller 90 can be realized in the personal computer PC and disposed inside of the personal computer PC. The evaluator makes evaluations observing the moving screen on the display unit 82 and inputs the evaluation results from the input unit 81. The input evaluation results are recorded in the evaluation result recording unit 83B of the storage unit 83. In the present invention, an aspect where the physical property is determined by the human (for example, the evaluator) is also possible (see a fourth embodiment).

Figure 3:
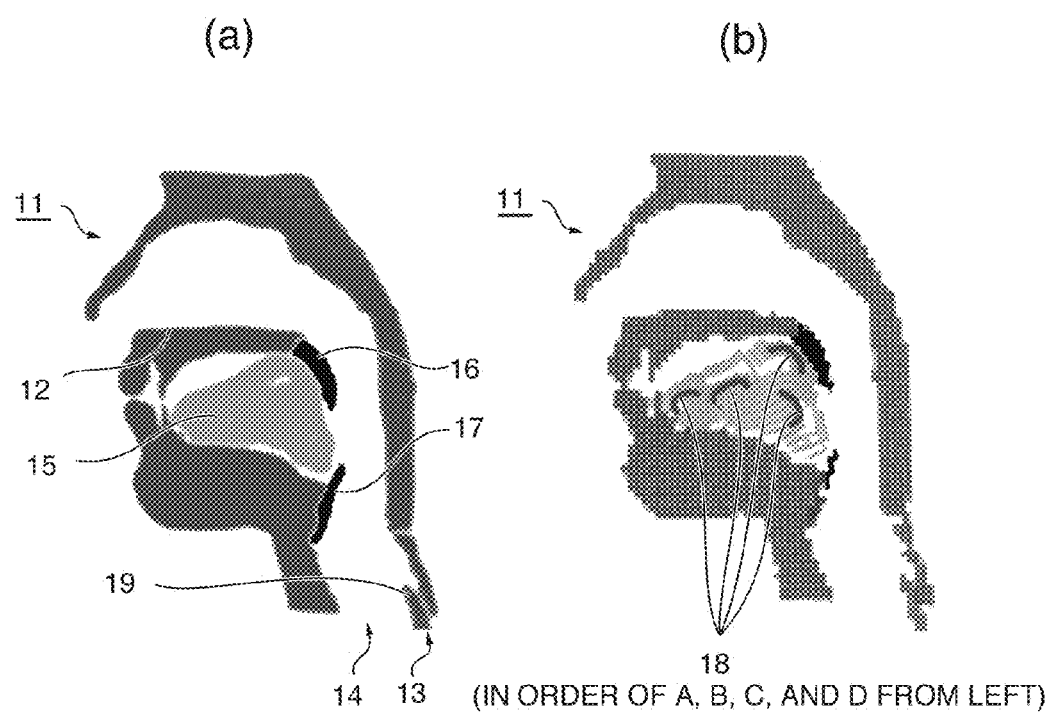
FIG. 3 illustrates an exemplary oral cavity model.

FIG. 3 illustrates the exemplary oral cavity model 11. FIG. 3(*a*) illustrates a movable portion in the model. FIG. 3(*b*) illustrates a moving wall 18 (performs a peristaltic movement) portion of the tongue 15 in the model. In the embodiment, an exemplary peristaltic movement by the four moving walls 18 is illustrated. The oral cavity modeling unit 10 forms the oral cavity model 11 formed of oral cavity organs including, the oral cavity wall 12, the gullet 13 (entrance portion is illustrated), the respiratory tract 14 (entrance portion is illustrated), the tongue 15, the soft palate 16, and the epiglottis 17 and the like. The organ properties of each of the oral cavity organs (classification of rigid body, elastic body, plastic body, viscous body, powder, fluid or the like and physical property such as elastic modulus and degree of viscosity) are set by the organ property setting unit 20. For simplification, the tongue 15, the soft palate 16, the epiglottis 17, and the gullet 13 entrance are set as an elastic body while the others are set as a rigid body. The movements of the oral cavity organs (such as a reciprocation, a rotational movement, a peristaltic movement and the like) are set by the organ movement setting unit 30. For simplification, the movement of the tongue 15 is expressed by the peristaltic movement, those of the soft palate 16 and the epiglottis 17 are expressed by reciprocation at the base and rotational movement around the base, and the entrance portion of the gullet 13 is expressed by the reciprocations in the perpendicular direction to the central axis of the gullet 13. The wave movement can be used instead of the peristaltic movement.

Now returning to FIG. 2, as the target for the swallowing simulation, a medicinal product, a nonmedicinal product can be used as well as a food product ("the food product, the medicinal product, or the nonmedicinal product" is referred to as a "food product or similar product"). When the food product or similar product is liquid, the food product physical property setting unit 40 sets physical properties such as a fluid volume, a degree of viscosity, a surface tension, a specific gravity and the like. When the food product or similar product is a solid, the food product physical property setting unit 40 sets physical properties such as a shape, dimensions, an elastic modulus, tensile strength, a yield point, yield point stress, shear rate dependence of degree of viscosity, dynamic viscoelasticity, static viscoelasticity, compressive stress, breaking stress, breaking strain, hardness, adhesiveness, cohesiveness and the like. When the food product or similar product is a semisolid (with plasticity but without fluidity), the food product physical property setting unit 40 sets physical properties such as an amount, a degree of viscosity, a specific gravity, a yield point, yield point stress, shear rate dependence of degree of viscosity, dynamic viscoelasticity, static viscoelasticity, compressive stress, adhesiveness, cohesiveness and the like.

The input unit 81 is configured of an input device such as the computer mouse, the keyboard and the like. The input unit 81 injects a pseudo food product to be injected in the oral cavity. The computer mouse pointer, for example, is dragged in the oral cavity, an injection position of the pseudo food product in the oral cavity is, for example, set near the teeth in the oral cavity (for example, within ½ length of the pseudo food product), and time immediately after the dragging is set as injection time.

The movement analysis unit 50 analyzes a behavior of the pseudo food product while being swallowed in association with movements of the oral cavity organs. The movement of the tongue 15 is expressed by the peristaltic movement or a wave movement, and the movements of soft palate 16 and the epiglottis 17 are expressed by reciprocation at the base and rotational movement around the base. The reciprocation of the gullet 13 entrance moves the food product or similar product injected in the oral cavity. The movement of the food product or similar product is analyzed using the particle method. The food product or similar product is treated as particles in any forms of solid, semisolid, and liquid.

The display unit 82 displays an analysis result of the behavior of the food product or similar product on the moving screen. One exposure of the moving image can be displayed as a still image. Tracing back the time and displaying the moving images while being rewound are also possible. The storage unit 83 stores an oral cavity model, organ properties, a setting condition, an analysis result, an evaluation result and the like.

The evaluation is made by the evaluator viewing the moving screen on the display unit 82. "Good", "poor", a rank, a score, or similar evaluation is input to a cell in an evaluation table displayed on the display unit 82, for example. The evaluation result is recorded in the evaluation result recording unit 83B. An appropriate physical property value of the food product or similar product can be obtained by making evaluation while changing the physical property value of the food product or similar product by the food product physical property setting unit 40. The physical property determiner 70 automatically determines the physical property of the food product or similar product regarded as appropriate based on the evaluation result recorded in the evaluation result recording unit 83B. The number of physical properties may be a single or plural. The appropriate physical property may be, for example, indicated by creating a map showing an appropriate range, may be indicated by classification into a plurality of levels (for example, rank A to rank C), may be indicated by plurality of points, or may be indicated by an optimum one point. When many physical properties are to be obtained, the appropriate physical property range may be obtained using multidimensional analysis of principal component.

The controller 90 controls the swallowing simulation apparatus 100A and each unit of the swallowing simulation apparatus 100A to have functions required for the swallowing simulation apparatus 100A. The controller 90 includes a swallowing simulator (analysis software) in a built-in memory.

(Swallowing Simulator)

The swallowing simulator has been created using a general-purpose two-dimensional particle method analysis software "Physi-Cafe" (manufactured by Prometech Software, Inc.). A physical property value of a fluid and time, for example, cannot be directly input to the analysis software as a numerical value. However, dimensionless physical quantities of the physical property value of the fluid and time can be appropriately changed, featuring a high speed analysis by simplifying a qualitative analysis.

FIG. 3(a) illustrates a movable portion in the oral cavity model 11. FIG. 3(b) illustrates the moving wall 18 (performs a peristaltic movement) portion of the tongue 15 in the model. In the model, for simplification, only the four portions are set as the movable parts: the tongue 15, the soft palate 16, the epiglottis 17, and an entrance of the gullet 13. A mechanism of transporting a bolus rearward by the peristaltic movement is configured as follows. The four moving walls 18 are embedded in the tongue 15, which is an elastic body. Then, the movement is performed while changing an amplitude of oscillation at the same period and shifting a phase. In this model, the four moving walls 18 are set as the elastic body. The one moving wall 18 cannot achieve the peristaltic movement, the two moving walls 18 generates an awkward movement, the three or more moving walls 18 can express a smooth peristaltic movement. The five or more moving walls 18 increase a computational load whereas makes little difference in natural movement from the case where the three or four moving walls 18 are used. Accordingly, use of the three or four pieces is preferable. Thus, a simulation operation where the elastic body (tongue) autonomously deforms is achieved. Then, a forcible deformation of the elastic body, which is extremely difficult in a usual analysis, can be expressed. This respect is distinctive in numerical analysis (simulation). Additionally, as illustrated in FIG. 3(b), the pseudo food product and the tongue 15 are all constituted by particles, regardless of whether the pseudo food product or the tongue 15 is liquid or solid.

Table 1 illustrates movements of the movable parts. The main feature is that a movement amount of displacement and angle are provided by a function. In particular, use of a periodic function achieves consecutive simulations. A to D in Table 1 are moving walls and disposed in the order of A, B, C, and D from the left in FIG. 3(b).

(Analysis Case 1)

Figure 4:
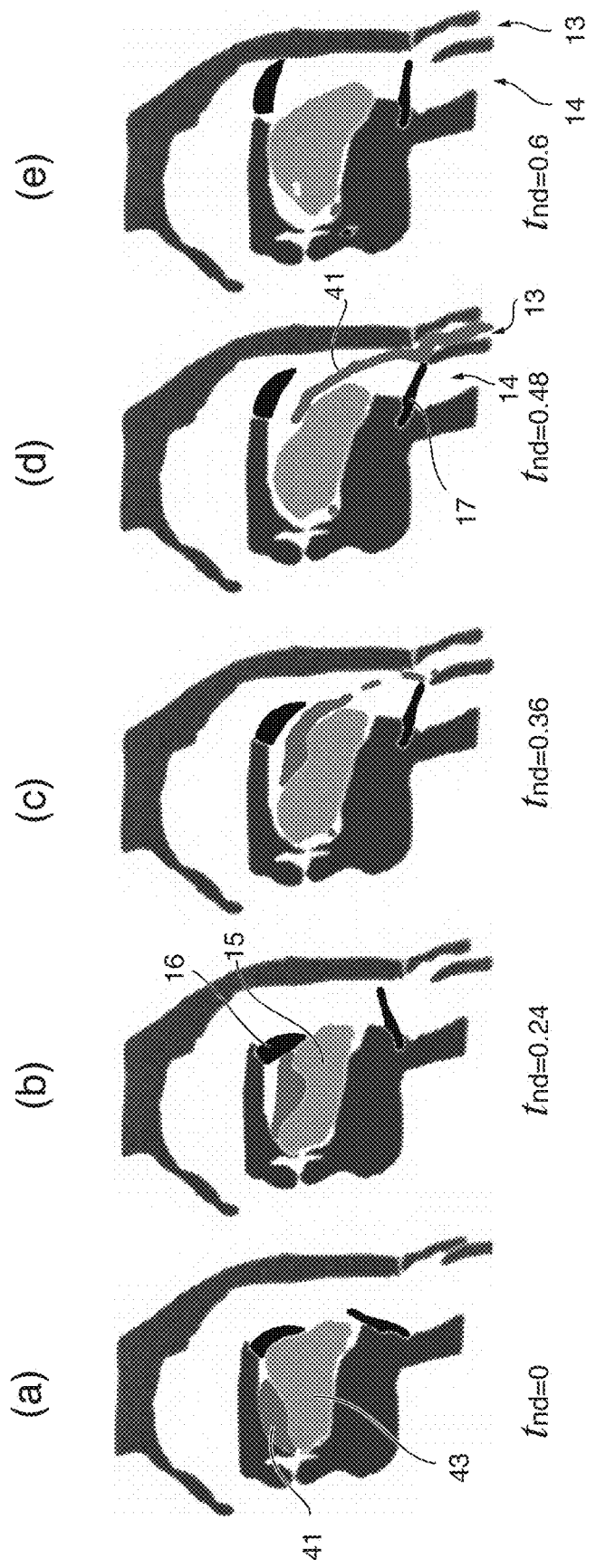
FIG. 4 simulatively illustrates a swallowing phenomenon of water.

FIG. 4 illustrates an exemplary analysis of a swallowing value experiment where water (assuming a degree of viscosity of 1 mPa·s) 41 is simulated. Here, a dimensionless swallowing period is denoted as $t_{nd}$. The $t_{nd}$ is what an analysis period taken for one swallowing (25 sec) is divided by a period taken for an actual swallowing phenomenon to complete (defined that the swallowing action is completed after an elapse of 1 sec from entrance of the water 41 in the mouth in this analysis).

The liquid (water) 41 that exists on the tongue 15 at $t_{nd}=0$ is held between the tongue 15 and the soft palate 16 at $t_{nd}=0.24$. At $t_{nd}=0.36$, it is seen that the soft palate 16 moves rearward and rotates to form a space for the liquid 41 to pass through whereas the soft palate 16 obstructs the passage from the nasal cavity. At $t_{nd}=0.48$, it is seen that the liquid 41 flows to the gullet 13 without entering the respiratory tract 14 lidded by the epiglottis 17. At $t_{nd}=0.6$, it is seen that the water 41 does not exist around the epiglottis 17 when the epiglottis 17 rises, thus accidental swallowing and accidental ingestion do not occur. It can also be observed from this result that a complicated fluid behavior involving a free surface, which was difficult to be expressed by the analysis method (lattice method) up to the present, can be expressed by the particle method.

(Analysis Case 2)

Figure 5:
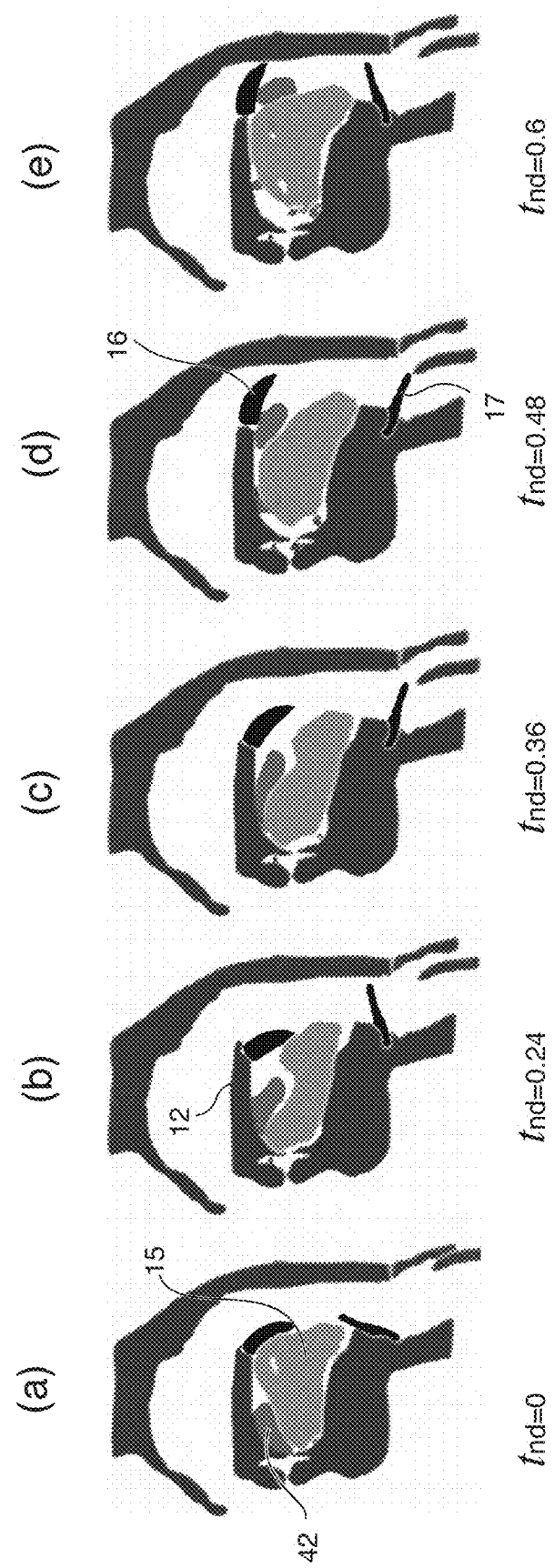
FIG. 5 simulatively illustrates the swallowing phenomenon of an adherent bolus (assume a rice cake).

FIG. 5 illustrates the simulation results of a bolus such as a rice cake 42 with high adhesiveness while being swallowed. The analysis software, which is the base of the simulator that has been developed this time, treats a physical property value, such as adhesiveness, as a relative value with a physical property value of a certain standard object, not an absolute value. Therefore, in the simulation, adhesiveness was appropriately changed (about 600 to 2300 J/m3) for analysis to the extent of adhering to a palate. The adherent bolus 42 that exists on the tongue 15 at $t_{nd}=0$ adheres to the oral cavity wall 12 (hard palate) at $t_{nd}=0.24$, and a rearward flow is not observed. At $t_{nd}=0.36$, it is seen that the bolus 42 is stretched while adhering to the palate in spite of the peristaltic movement of the tongue 15. At $t_{nd}=0.48$, it is seen that the bolus 42 adheres to the soft palate 16 and does not come out although being lidded by the epiglottis 17. Finally, even at $t_{nd}=0.6$, the adherent bolus 42 firmly adheres to the soft palate 16.

TABLE 1

THE RELATION BETWEEN MOVING PART AND MOVEMENT AMOUNT IN STANDARD MOTION

| MOVING PART | | X DIRECTION | Y DIRECTION | ROTATION |
|---|---|---|---|---|
| TONGUE | A | $-1 * \sin(t) - 0.5$ | $2 * \sin(t - 1)$ | — |
|  | B | $-3 * \sin(t)$ | $-3 * \sin(t) - 1$ | — |
|  | C | $-\sin(t - 1) - 1.0$ | $-4 * \sin(t - 1)$ | — |
|  | D | $-2.0 * \sin(t) - 2.0$ | $-2 * \sin(t - 3) + 2$ | — |
| SOFT PALATE | | $-2 * \sin(t)$ | 0 | $0.5 * \sin(t - 3)$ |
| EPIGLOTTIS | | $\sin(t + 1.2) - 0.8$ | $-\sin(t + 1.2) + 1$ | $0.8 * \sin(t + 1.2) - 0.6$ |
| GULLET WALL | | $-2 * \sin(t + 1.2)$ | $-2 * \sin(t + 1.2)$ | 0 |

The movement amount of each organ can be easily changed by changing a formula in Table 1 and a parameter of the formula. Specifically, the movement amount can be adjusted by changing an amplitude of a sine function. A speed and timing of the movement can be adjusted by changing the period and the phase. The simulator features a high degree of freedom in adjustment of each portion.

Figure 6:
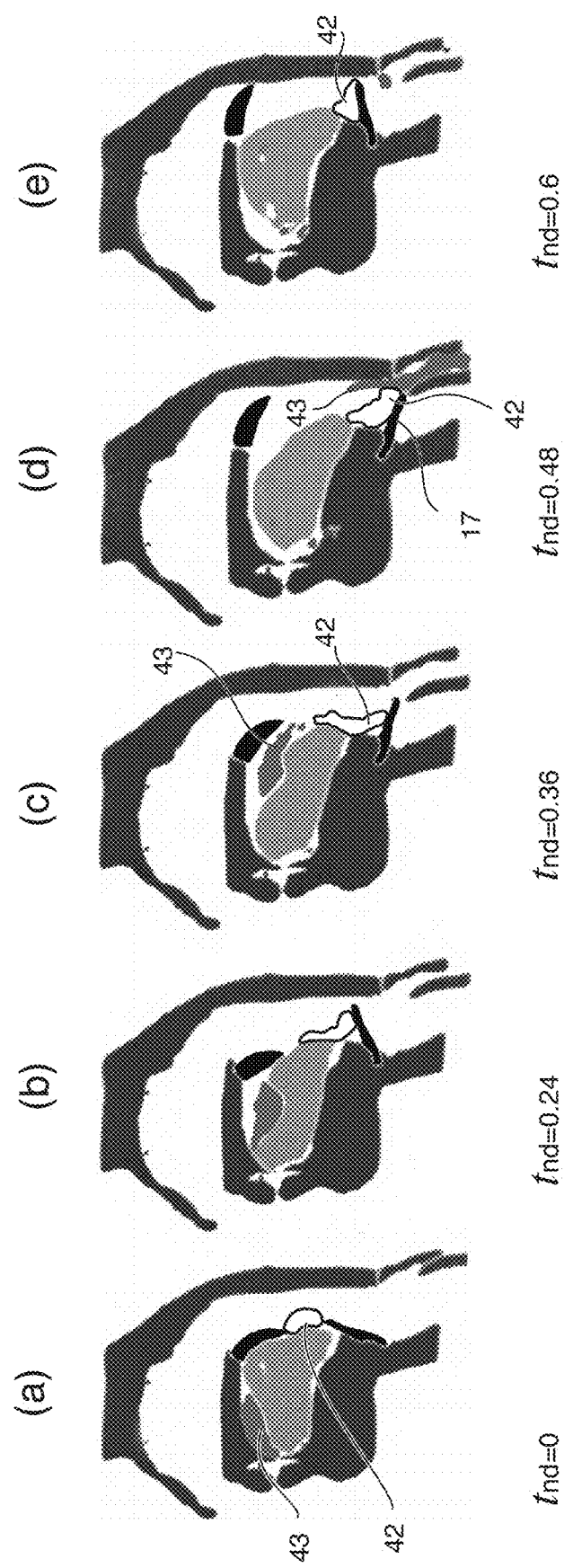
FIG. 6 simulatively illustrates the swallowing phenomenon when the adherent bolus obstructing near the soft palate is rinsed with water.

FIG. 6 illustrates a simulation result of a state where the adherent bolus 42 obstructs near the soft palate 16, rinse liquid (assuming water) 43 is run into the mouth, and the obstructing bolus 42 is washed away. At $t_{nd}=0.36$, the rinse water 43 being run into the mouth flows to the larynx. However, even at $t_{nd}=0.48$, the adherent bolus 42 remains at the epiglottis 17. Thus, it can be observed that washing away the adherent bolus 42 by one rinsing is difficult. This simulator also confirmed that, similarly to the actual phenomenon, the bolus with high adhesiveness needs to be rinsed by plural times.

Thus, the simulator can couple the two or more liquid, solid, and semisolid boluses or fluids with different degree of viscosity, adhesiveness, a surface tension, or similar physical property for solution. Coupled analyses of liquid-liquid, liquid-solid, and solid-solid with free surface and different physical property have been extremely difficult up to the present. However, use of the particle method facilitates qualitative analysis.

(Analysis Case 3)

Figure 7:
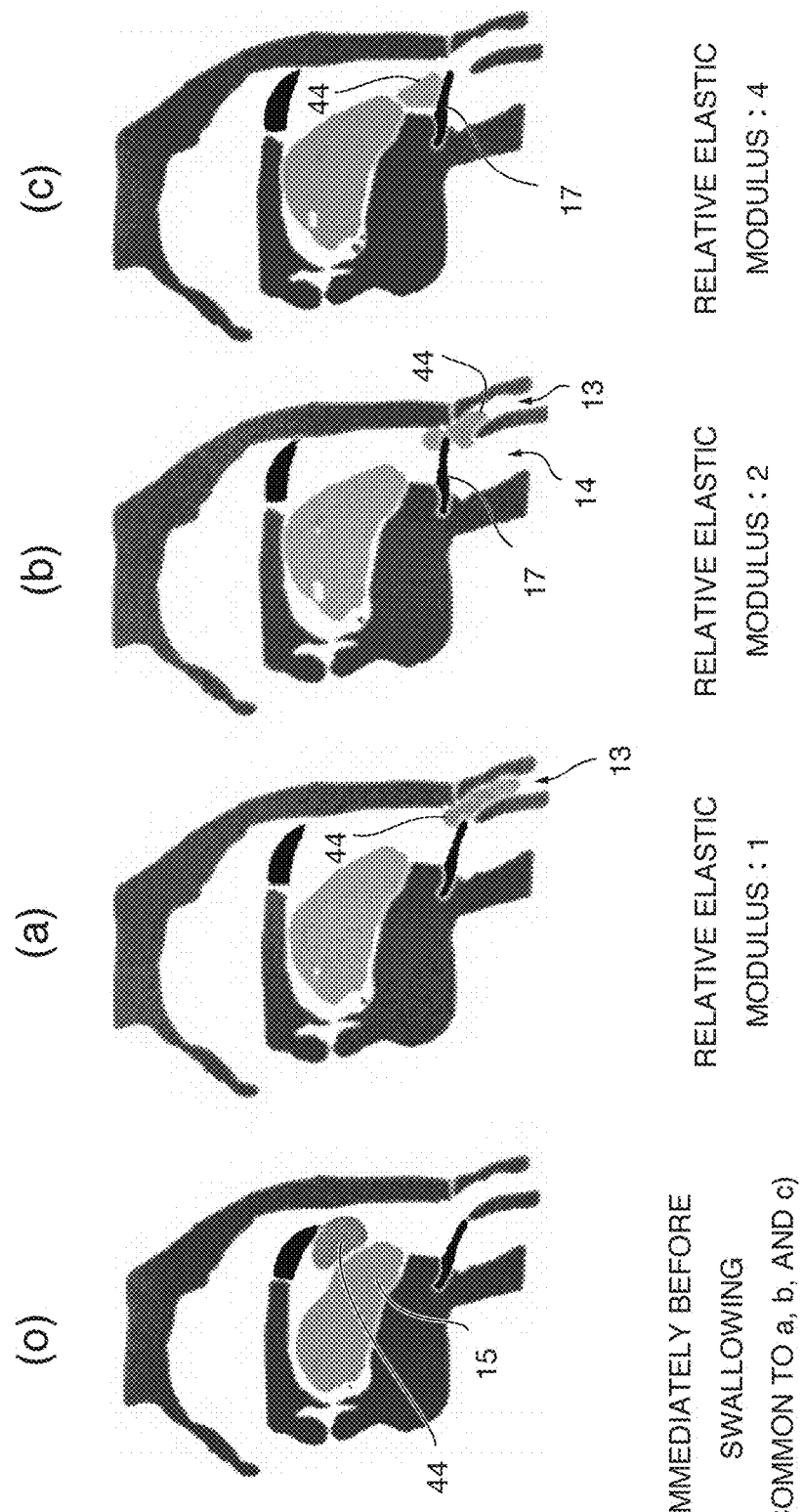
FIG. 7 illustrates swallowing simulation results of a jelly-like bolus.

FIG. 7 illustrates a simulation result when the bolus 44 that can be broken under a certain amount of constant force, such as a jelly, is being swallowed. Here, hardness of the bolus 44 is expressed using a relative elastic modulus, which is a relative ratio with a standard bolus. Shapes of the boluses 44 immediately before being swallowed are all same.

FIG. 7(*o*) illustrates a state immediately before the swallowing. FIG. 7(*a*) illustrates a case where the relative elastic modulus of the bolus 44 is low (relative elastic modulus=1). It can be seen that the bolus 44 deforms along the shape of the gullet 13 at the moment of entrance to the gullet 13 and then flows. FIG. 7(*b*) illustrates a case where the relative elastic modulus of the bolus 44 is medium (relative elastic modulus=2). FIG. 7(*b*) shows a moment where the bolus 44 fails to deform to the shape of the gullet 13, and the bolus 44, which is out of the gullet 13, is sandwiched between the gullet 13 and the epiglottis 17, and cut into strips. Entrance of the bolus 44, which is cut into pieces, to the respiratory tract 14 causes accidental swallowing and accidental ingestion. That is, even if the bolus 44 is soft to some extent, there is a possibility of a risk of accidental swallowing or accidental ingestion if the bolus 44 cannot deform to a size that enters the gullet 13. FIG. 7(*c*) illustrates a case where the relative elastic modulus of the bolus 44 is high (relative elastic modulus=4). Since the bolus 44 has high relative elastic modulus, the shape of the bolus 44 hardly deforms. Obstruction at the epiglottis 17 or a flow to the respiratory tract 14 was able to be estimated.

In the actual phenomenon as well, the experience of choking accidents involving konjac jelly or similar incidents clarifies importance of a size and hardness of a product to prevent an accident of suffocation. Based on a fact that the similar trend was obtained in this simulation result, this suggests a possible use of the simulator using the particle method for the swallowing simulation of a jelly-like bolus.

(Analysis Case 4)

Some functional deteriorations in a human body probably cause an accidental swallowing and accidental ingestion. A human body was simulated and examined for some functional deteriorations.

Table 2 illustrates simulation conditions of when a movement of the epiglottis 17 became slow. Specifically, an amplitude of movement of the epiglottis 17 was decreased (to the half) in the rotation direction.

TABLE 2

THE RELATION BETWEEN MOVING PART AND MOVEMENT AMOUNT WHEN A MOVEMENT OF THE EPIGLOTTIS BECAME SLOW

| MOVING PART | | X DIRECTION | Y DIRECTION | ROTATION |
|---|---|---|---|---|
| TONGUE | A | $-1 * \sin(t) - 0.5$ | $2 * \sin(t - 1)$ | — |
| | B | $-3 * \sin(t)$ | $-3 * \sin(t) - 1$ | — |
| | C | $-\sin(t - 1) - 1.0$ | $-4 * \sin(t - 1)$ | — |
| | D | $-2.0 * \sin(t) - 2.0$ | $-2*\sin(t - 3) + 2$ | — |
| SOFT PALATE | | $-2 * \sin(t)$ | 0 | $0.5 * \sin(t - 3)$ |
| EPIGLOTTIS | | $\sin(t + 1.2) - 0.8$ | $-\sin(t + 1.2) + 1$ | $0.4 * \sin(t + 1.2) - 0.3$ |
| GULLET WALL | | $-2 * \sin(t + 1.2)$ | $-2 * \sin(t + 1.2)$ | 0 |

Figure 8:
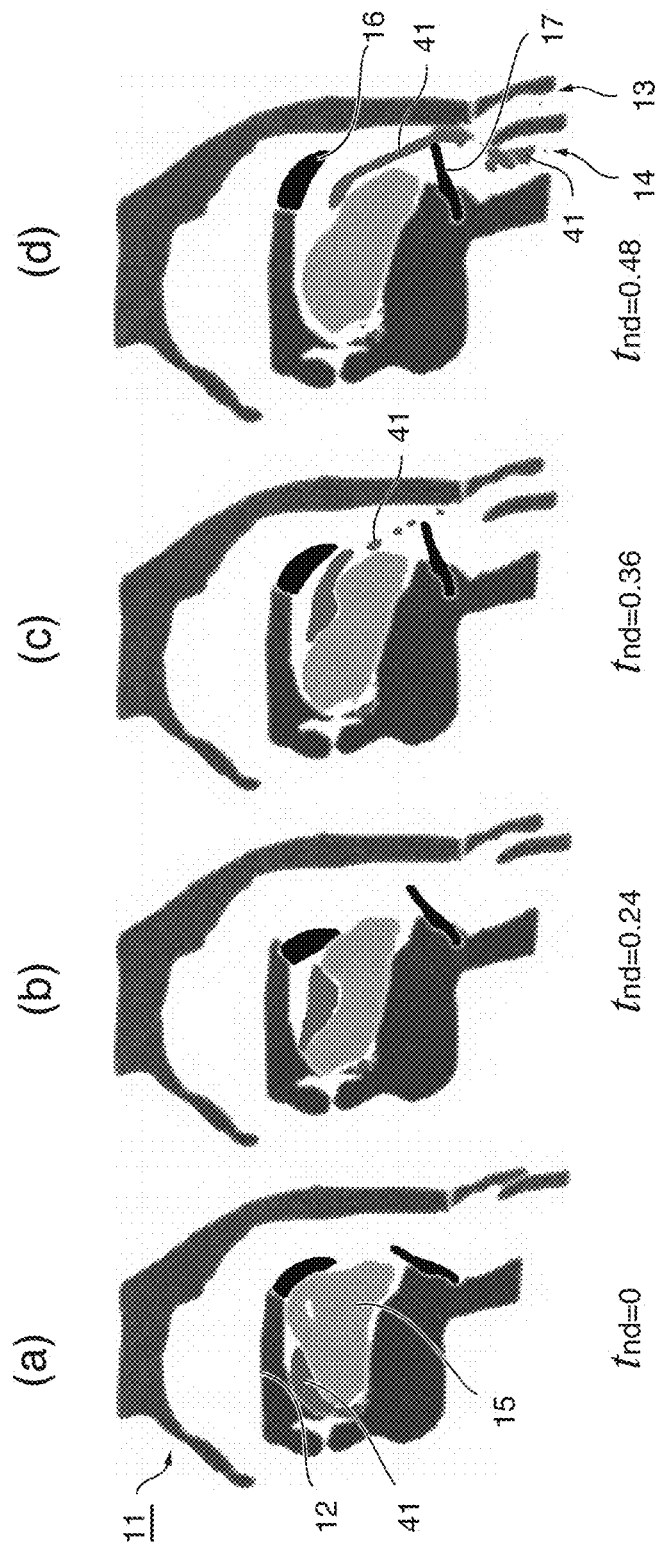
FIG. 8 simulatively illustrates the swallowing phenomenon in the case where a movement of an epiglottis is slow.

FIG. 8 illustrates the simulation results of the case where the movement of the epiglottis 17 became slow. As seen from comparison with FIG. 4, in FIG. 4, at $t_{nd}$=0.48, the epiglottis 17 completely "lids" the respiratory tract 14 to prevent a flow of the liquid 41 to the respiratory tract 14. However, it is recognized that in FIG. 8, where functional restriction is made, the epiglottis 17 does not function and most of the water 41 is accidentally ingested to the respiratory tract 14.

Table 3 illustrates analysis conditions where a movement amount of the entrance portion of the gullet 13 is small. Specifically, a moving speed of the gullet wall that walls the gullet 13 and the respiratory tract 14 is set slow (to the half).

TABLE 3

THE RELATION BETWEEN MOVING PART AND MOVEMENT AMOUNT WHEN A MOVEMENT AMOUNT OF THE ENTRANCE PORTION OF THE GULLET IS SMALL

| MOVING PART | | X DIRECTION | Y DIRECTION | ROTATION |
|---|---|---|---|---|
| TONGUE | A | $-1 * \sin(t) - 0.5$ | $2 * \sin(t - 1)$ | — |
| | B | $-3 * \sin(t)$ | $-3 * \sin(t) - 1$ | — |
| | C | $-\sin(t - 1) - 1.0$ | $-4 * \sin(t - 1)$ | — |
| | D | $-2.0 * \sin(t) - 2.0$ | $-2 * \sin(t - 3) + 2$ | — |
| SOFT PALATE | | $-2 * \sin(t)$ | 0 | $0.5 * \sin(t - 3)$ |
| EPIGLOTTIS | | $\sin(t + 1.2) - 0.8$ | $-\sin(t + 1.2) + 1$ | $0.8 * \sin(t + 1.2) - 0.6$ |
| GULLET WALL | | $1 * \sin(t + 1.2)$ | $-1 * \sin(t + 1.2)$ | 0 |

Figure 9:
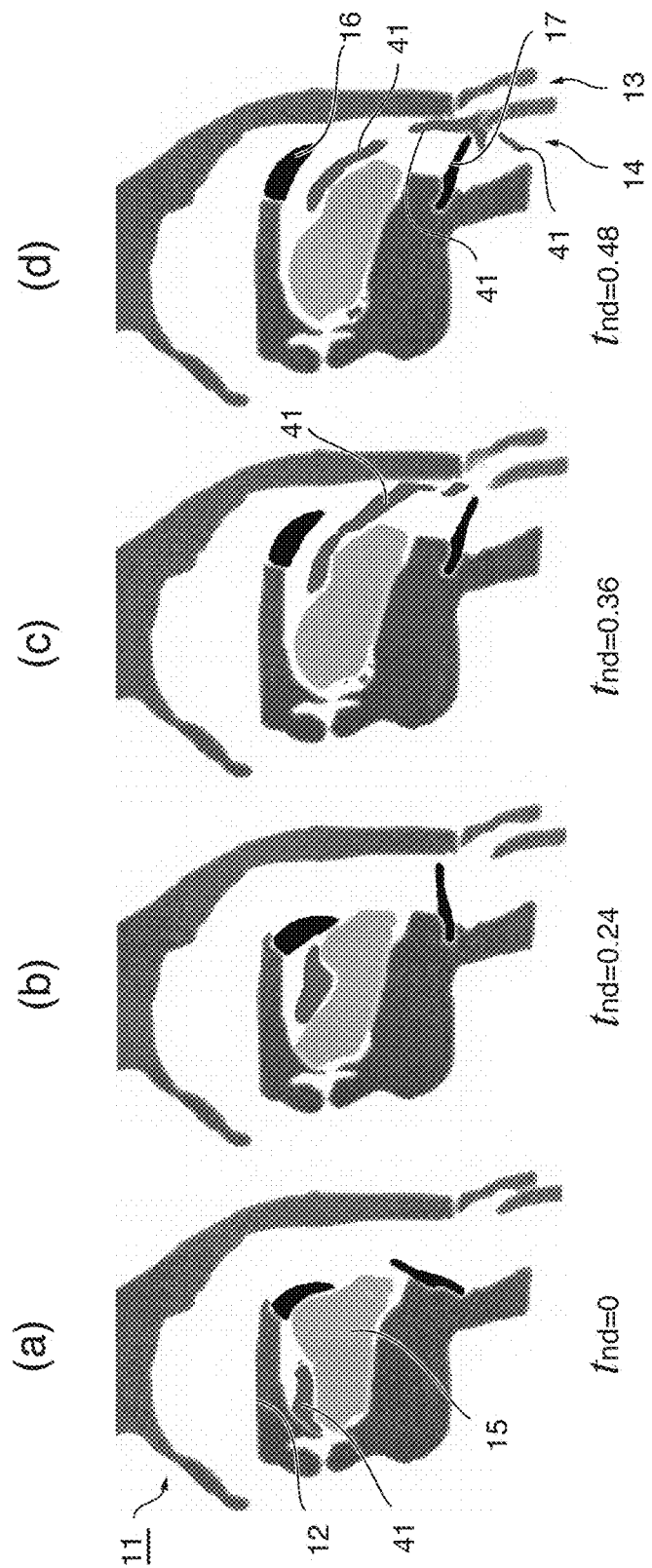
FIG. 9 simulatively illustrates the swallowing phenomenon in the case where a movement of a boundary surface between a gullet and a respiratory tract is slow.

FIG. 9 illustrates the simulation results. As seen from comparison with FIG. 4, in FIG. 4, at $t_{nd}$=0.48, the epiglottis 17 completely "lids" the respiratory tract 14 to prevent a flow of the liquid 41 to the respiratory tract 14. However, in FIG. 9, where functional restriction is made, the following can be observed. The epiglottis 17 cannot completely close the respiratory tract 14. Then the half of the water 41 flows to the respiratory tract 14, causing accidental ingestion (accidental inspiration). Thus, a functional deterioration causing an accidental swallowing and accidental ingestion can be examined simulatively with simple setting change.

As described above, the simulator allows analysis of a behavior of the various food product or similar product while being swallowed. A three dimensional analysis is required for quantitative examination. However, in either two dimension or three dimension, the particle method is superior in that these swallowing phenomena are revealed. This respect is advantages in the case where the particle method is applied to the swallowing simulator.

Figure 10:
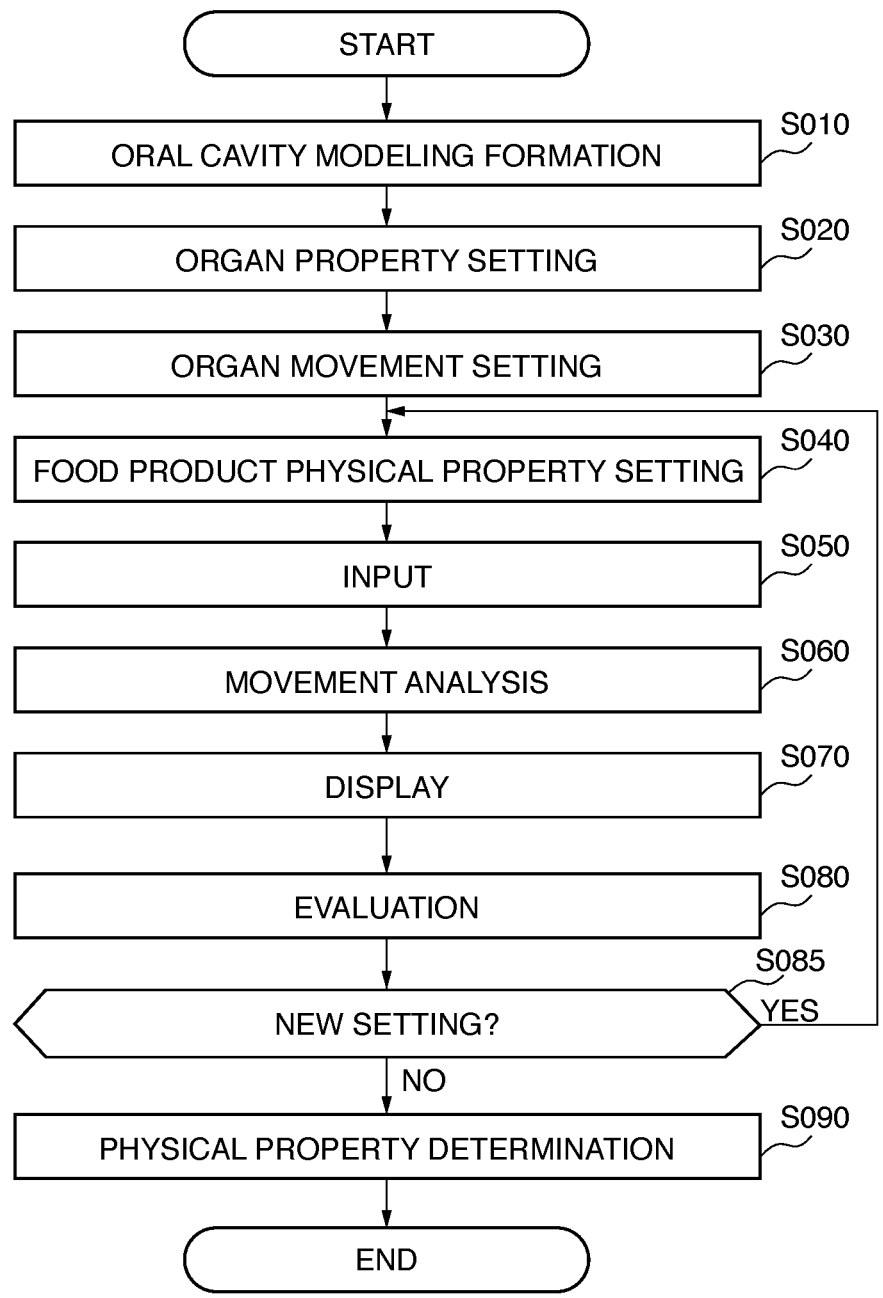
FIG. 10 illustrates an exemplary processing flow of the swallowing simulation method according to the first embodiment.

FIG. 10 illustrates an exemplary processing flow of the swallowing simulation method according to the first embodiment. First, the oral cavity model 11 formed of oral cavity organs is formed (S010: oral cavity modeling step). Next, an organ property of each of the oral cavity organs in the oral cavity model 11 is set (S020: organ property setting step). Next, a movement of each of the oral cavity organs in the oral cavity model 11 is set (S030: organ movement setting step). Next, the food product or similar product as an analysis target and a physical property of the food product or similar product are set (S040: food product physical property setting step). These setting contents can be freely selected according to the condition. The setting contents are stored to the storage unit 83. Next, the pseudo food products 41 to 44 formed by modeling the food product are input to the oral cavity (S050: input step). The pseudo food products 41 to 44 are input, for example, by dragging the cursor in the oral cavity with the computer mouse by the evaluator. Next, a movement of each of the oral cavity organs and behaviors of the pseudo food products 41 to 44 while being swallowed in the oral cavity model 11 are analyzed using the particle method (S060: movement analysis step). An MSP method, for example, can be used. Next, analysis results obtained in the movement analysis step (S060) are displayed (S070: display step). Next, easiness of eating and/or easiness of drinking of the food product are evaluated based on the analysis result of the behavior of the pseudo food product 41 while being swallowed (S080: evaluation step). Evaluation is made by the evaluator while viewing the moving screen on the display unit 82. "Good", "poor", a rank, a score, or similar evaluation is input to a cell in an evaluation table displayed on the display unit 82, for example. After the evaluation, the step is returned to the food product physical property setting step (S040), the physical property of the food product is changed and set, and then the subsequent steps are repeatedly performed to the evaluation step. A physical property value to be changed can be freely selected by determination of the evaluator. However, when an appropriate physical property is found at the first trial, the subsequent settings and evaluations may be omitted. Next, the physical property of the food product determined as appropriate in the evaluation step (S080) is determined (S090: physical property determination step). Here, an appropriate physical property range may be indicated, an appropriate physical property may be classified into ranks, or an optimum value may be selected.

Evaluation items are, for example, as follows.
(a) Whether the swallowing, the accidental swallowing or accidental ingestion risk (the food product adheres to the palate wall and difficult to be peeled off, obstructs the throat or the gullet, or enters the respiratory tract) exists or not
(b) How long is the swallowing period? Is the threshold exceeded?
(c) How much are stress and shear stress applied to the throat wall? Is the threshold exceeded?
(d) Based on (a) to (c), considering correlativity with a sensory evaluation (tasty, exhilarating feeling, or similar feeling) whose data has been obtained separately, easiness of drinking, easiness of eating, difficulty of drinking, and difficulty of eating are evaluated comprehensively As described above, according to the embodiment, the organ properties, the movements of the oral cavity organs, and the physical property of the food product are set about the oral cavity model 11. Then, the behavior of the food product is analyzed using the particle method. This allows to analyze a phenomenon of swallowing using the swallowing simulation method that facilitates reproduction of the actual phenomenon of swallowing.

Second Embodiment

In the first embodiment, an exemplary swallowing evaluation made by inputting the food product and viewing the moving image by the evaluator is described. In the second embodiment, an example where the swallowing simulation apparatus automatically inputs the food product based on the setting and automatically performs the swallowing evaluation is described. The following mainly describes the points different from the first embodiment (similarly, in the following embodiments, the points different from an antecedent embodiment are mainly described).

Figure 11:
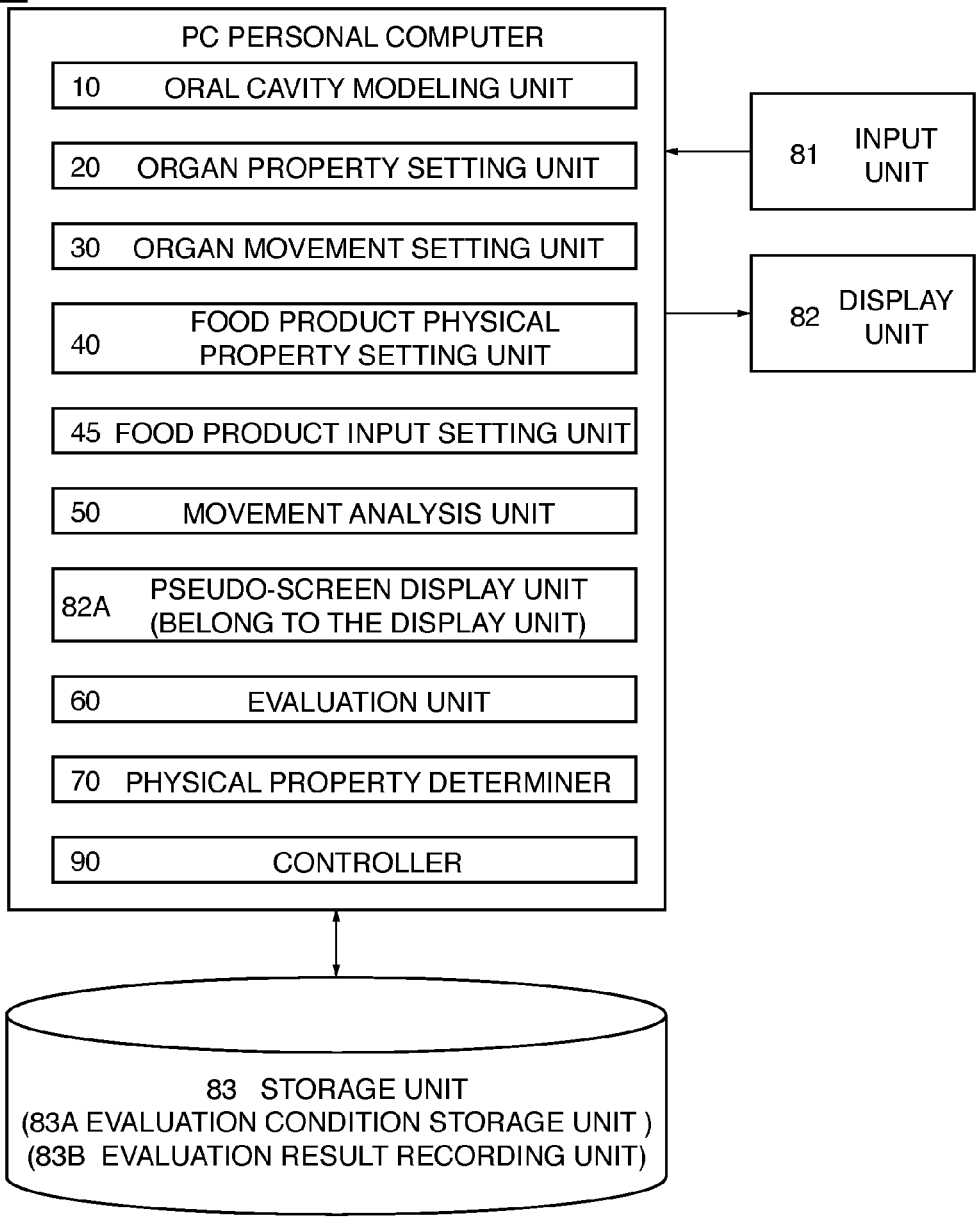
FIG. 11 illustrates an exemplary configuration of a swallowing simulation apparatus according to a second embodiment.

FIG. 11 illustrates an exemplary configuration of the swallowing simulation apparatus 100B according to the second embodiment. An evaluation unit 60, the pseudo screen display unit 82A, and the food product input setting unit 45 are added in the personal computer (PC) compared with the first embodiment (see FIG. 2). The evaluation unit 60 automatically evaluates easiness of eating and/or easiness of drinking of the food product. The pseudo screen display unit 82A displays the analysis result of the behavior of the pseudo food product while being swallowed on the virtual moving screen. The food product input setting unit 45 sets an input condition of the pseudo food product. The evaluation condition storage unit 83A is added in the storage unit 83. The evaluation condition storage unit 83A stores an evaluation condition. Other configurations are same to the first embodiment.

Figure 12:
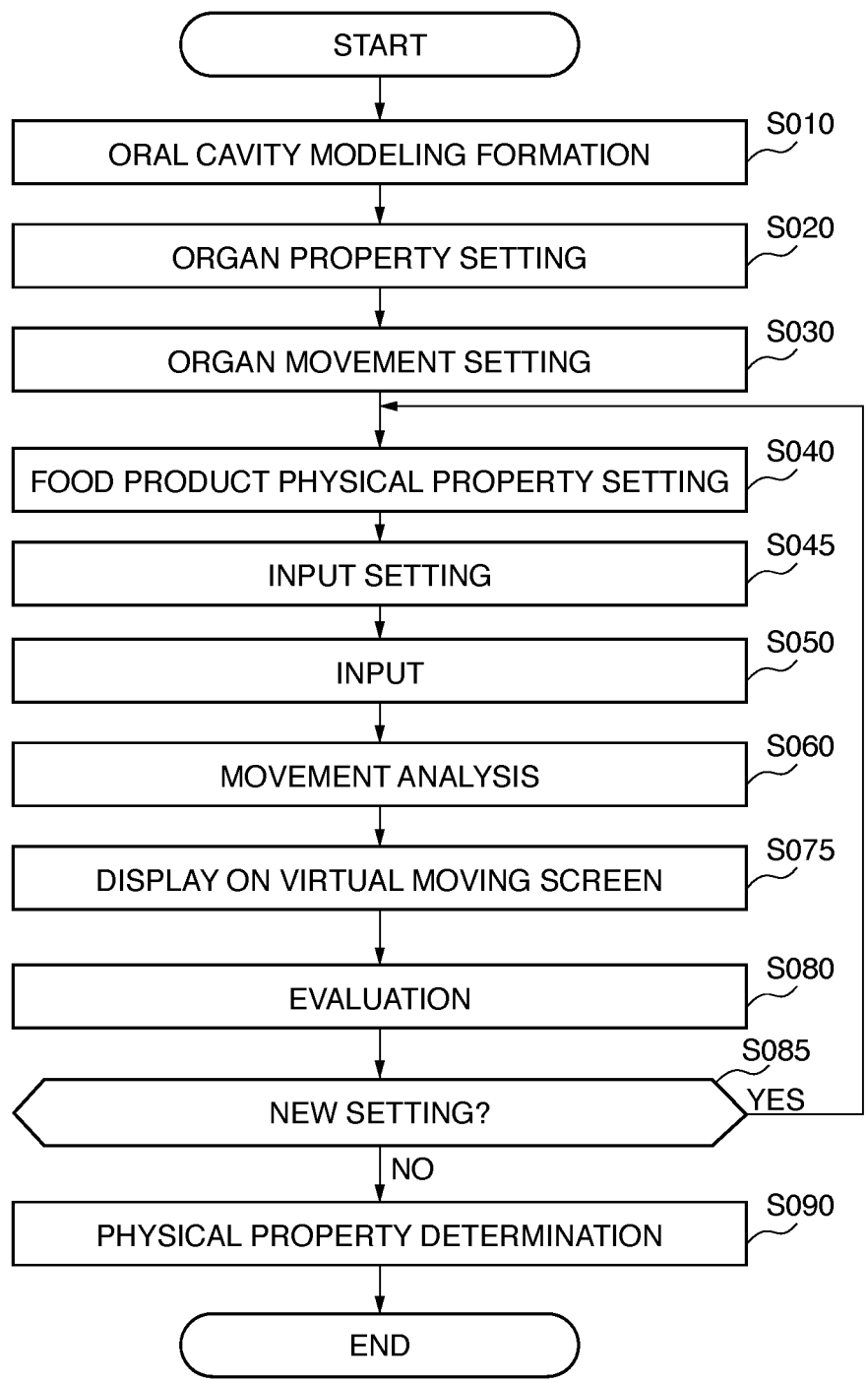
FIG. 12 illustrates an exemplary processing flow of the swallowing simulation method according to the second embodiment.
Figure 13:
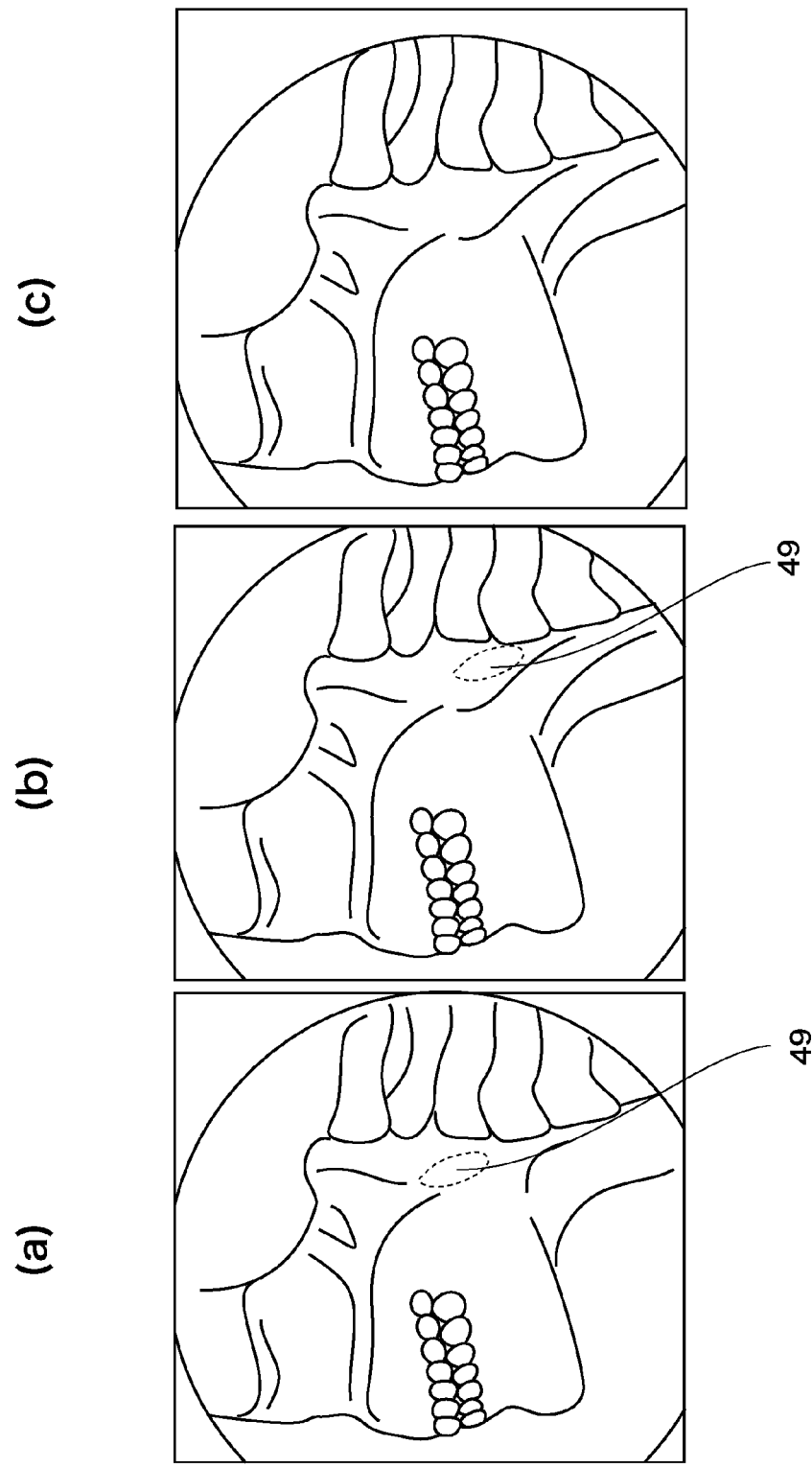
FIG. 13 illustrates an exemplary videofluoroscopic swallowing.
Figure 14:
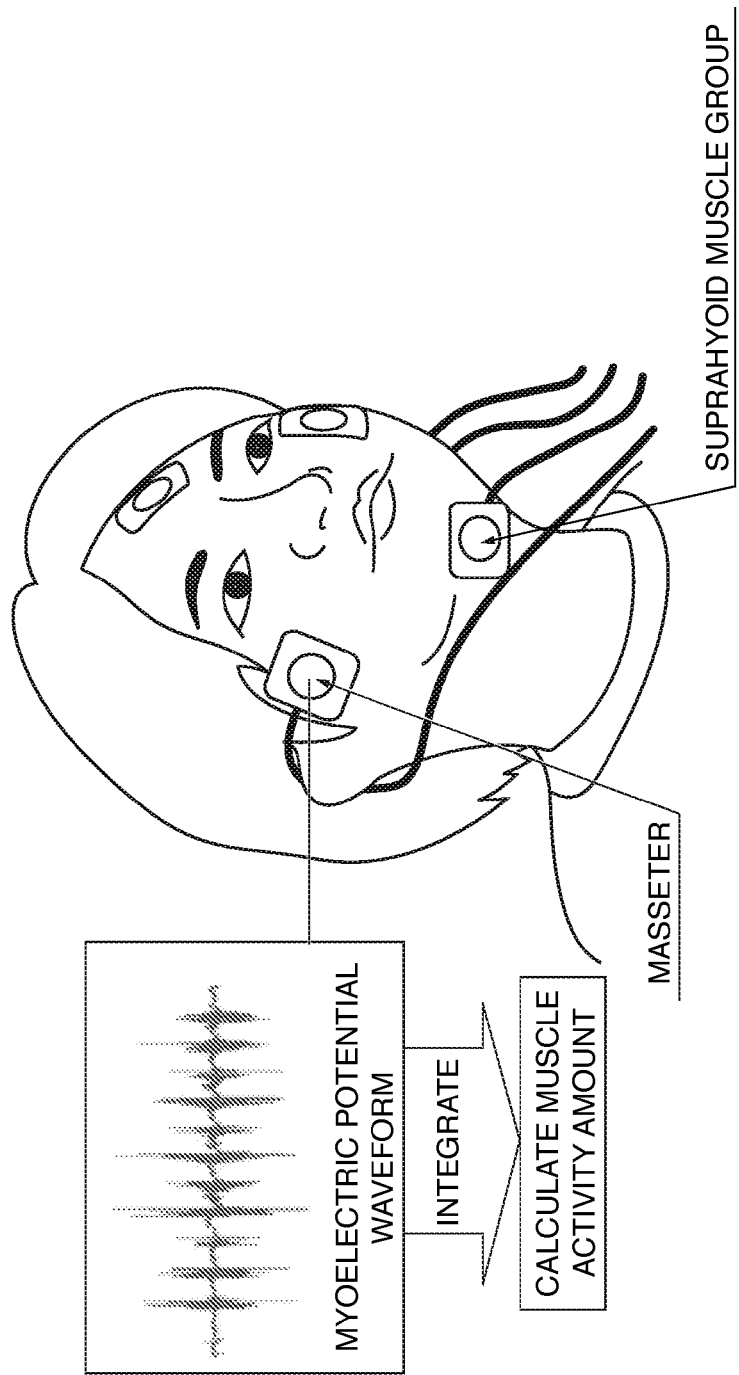
FIG. 14 illustrates an exemplary myoelectric potential measurement.

FIG. 12 illustrates an exemplary processing flow of the swallowing simulation method. A food product input setting step (S045) is added before the input step (S050) compared with the first embodiment (see FIG. 10). The food product input setting step (S045) sets the input condition of the food product. The display step (S070) for displaying the moving screen on the display unit 82 is replaced by the step for displaying the virtual moving screen on the pseudo screen display unit 82A (S075). In the evaluation step (S080), the evaluation unit 60 makes an automatic evaluation. Other steps are same to the first embodiment.

In the second embodiment, an injection position and injection timing of the food product are preset to the food product input setting unit 45 (S045: food product input setting step). The injection position of the pseudo food product in the oral cavity is, for example, set near the teeth in the oral cavity (for example, within ½ length of the pseudo food product). Next, the pseudo food product is injected in the oral cavity in accordance with the setting conditions (position and timing) (S050: input step). For automatic evaluation, the evaluation condition is preliminarily stored to the evaluation condition storage unit 83A. The behaviors of the oral cavity model 11 and the pseudo food product 41 as the analysis results of the simulations are displayed on the virtual moving screen of the pseudo screen display unit 82A in the personal computer PC. The display of the pseudo screen display unit 82A is collated with the evaluation condition of the evaluation condition storage unit 83A by the evaluation unit 60. Thus, evaluation is performed.

Evaluation items are, for example, as follows.
(a) Whether a swallowing, an accidental swallowing or an accidental ingestion risk (the food product adheres to the palate wall or the like and difficult to be peeled off, obstructs the throat or the gullet, or enters the respiratory tract) exists or not
(b) How long is the swallowing period? Is the threshold exceeded?
(c) How much are stress or shear stress applied to the throat wall? Is the threshold exceeded?
(d) Based on (a) to (c), considering correlativity with a sensory evaluation (tasty, exhilarating feeling, or similar feeling) whose data has been obtained separately, easiness of drinking, easiness of eating, difficulty of drinking, or difficulty of eating is evaluated comprehensively. (a) to (c) and the sensory evaluations are preliminarily converted into values, respectively. Then, the values are multiplied by a weighting factor and are summed. The total is automatically and comprehensively evaluated. (c) and the sensory evaluation may be omitted.

Other configurations and processing flows are same to the first embodiment. Similarly to the first embodiment, this allows to analyze a phenomenon of swallowing using the swallowing simulation method that facilitate reproduction of the actual phenomenon of swallowing.

Additionally, even the case where one of the input and the evaluation is performed by the human and the other is performed by the computer is similarly applicable and similar effects can be achieved.

Third Embodiment

While in the above described embodiments, an example of evaluation by the evaluator and an example of automatic evaluation by the swallowing simulation apparatus are described, the evaluation result (partial or overall evaluation result) may be displayed on the swallowing simulation apparatus for requesting the evaluator to evaluate. Regarding a processing flow, in the evaluation step (S080) of the second embodiment, the evaluation result (partial or overall evaluation result) by the swallowing simulation apparatus is displayed on the display unit 82 together with the evaluation table. With reference to the evaluation result by the swallowing simulation apparatus, the evaluator inputs his/her evaluation result on the evaluation table. The input step (S050) may be manually input by the human or may be automatically input. Other apparatus configurations and processing flows are same to the second embodiment. Similarly to the second embodiment, the swallowing simulation apparatus and the swallowing simulation method that facilitate reproduction of the actual phenomenon of swallowing can be provided.

Fourth Embodiment

In the above described embodiments, the physical property of the food product or similar product automatically determined as appropriate by the physical property determiner 70 is described as an example. In this embodiment, an exemplary determination made by the human is described. In the apparatus configuration of the embodiment, typically, the physical property determiner 70 in FIG. 2 of the first embodiment is removed. FIG. 10 can be used as an exemplary processing flow. The physical property determiner 70 may be present. In this case, the physical property determiner 70 is not used or a determination result by the physical property determiner 70 is shown to a decider (for example, the evaluator) as a reference. The physical property of the food product or similar product is determined as appropriate by the human. However, there is no difference in that the determination is made based on the evaluation result. Although, the determination is possibly slightly changed in an intellectual process, almost similar results are predicted. Other apparatus configurations and processing flows are same to the first embodiment. Similarly to the first embodiment, the swallowing simulation apparatus and the swallowing simulation method that facilitate reproduction of the actual phenomenon of swallowing can be provided. When a determination is made by the human, this applies to the second embodiment and the third embodiment similarly to the first embodiment.

Fifth Embodiment (Diagnosis Assistance)

In this embodiment, an exemplary application of the swallowing simulator according to the present invention to assistance for swallowing diagnosis is described.

Figure 15:
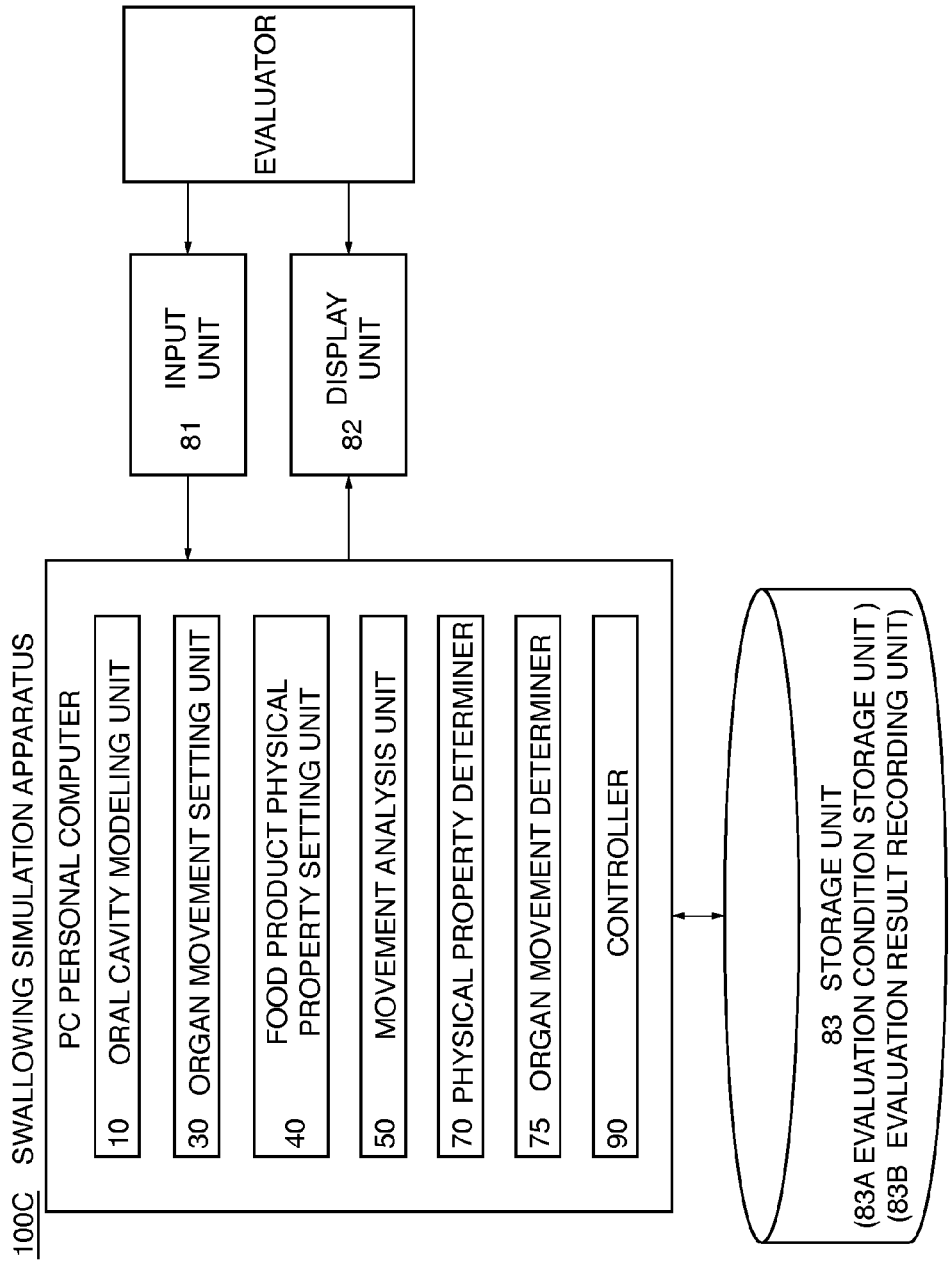
FIG. 15 illustrates an exemplary configuration of a swallowing simulation apparatus according to a fifth embodiment.

FIG. 15 illustrates a configuration of a swallowing simulation apparatus 100C according to the embodiment. An organ movement determiner 75 and a determination organ movement condition recording unit 83E are added to, and the organ property setting unit 20 is removed from the swallowing simulation apparatus 100A according to the first embodiment (see FIG. 2). Additionally, the organ movement setting unit 30 is more frequently used. The organ movement setting unit 30 sets movement properties of each of the oral cavity organs related to the swallowing movement. For example, a rate of reaction, timing of contract and relax, contract distance, elasticity (flexibility) and the like of a genioglossus and other muscles related to the swallowing, or similar property are set as movement parameters. Then, the organ movement determiner 75 determines an organ movement parameter of each of the oral cavity organs based on simulation results, that is, the analysis results analyzed by the movement analysis unit 50. A slow traveling wave motion of the tongue, for example, takes time to reach the swallowing. A slow reaction of the epiglottis 17 possibly causes the food product or similar product to enter the respiratory tract 14 through the larynx, resulting in accidental swallowing. This allows obtaining the organ movement parameters for each of the oral cavity organs finely fitting a behavior and a symptom of each of the oral cavity organs of a patient or a person to be diagnosed for checkup. The determination organ movement condition recording unit 83E records the organ movement parameter obtained by the organ movement determiner 75.

Then, based on the results of the oral cavity model 11 and the swallowing simulation, for example, whether muscle of the patient or the person subject to checkup is functionally deteriorated in the swallowing or not is diagnosed, and it comes to be useful in treatment. Since the organ function is put more importance than the physical property of the food product or similar product in diagnosis, a loop process may not be performed on the physical property and the physical property may be fixed. Such simulation apparatus can also be incorporated into the swallowing diagnosis assistance apparatus. The swallowing diagnosis assistance apparatus with medical treatment diagnosis result database that records diagnosis result on the patient or the person subject to checkup is configured, for example. The diagnosis result recorded in the medical treatment diagnosis result database is compared with the evaluation result recorded in the evaluation result recording unit 83B of the swallowing simulation apparatus 100C. This allows finding a functionally deteriorated portion of each of the oral cavity organs, thus ensuring prompt diagnosis. This comparison can be, for example, performed by a diagnosis result comparator, allowing a doctor to refer to the comparison result and update the diagnosis result. The organ property setting unit 20 may be present.

Figure 16:
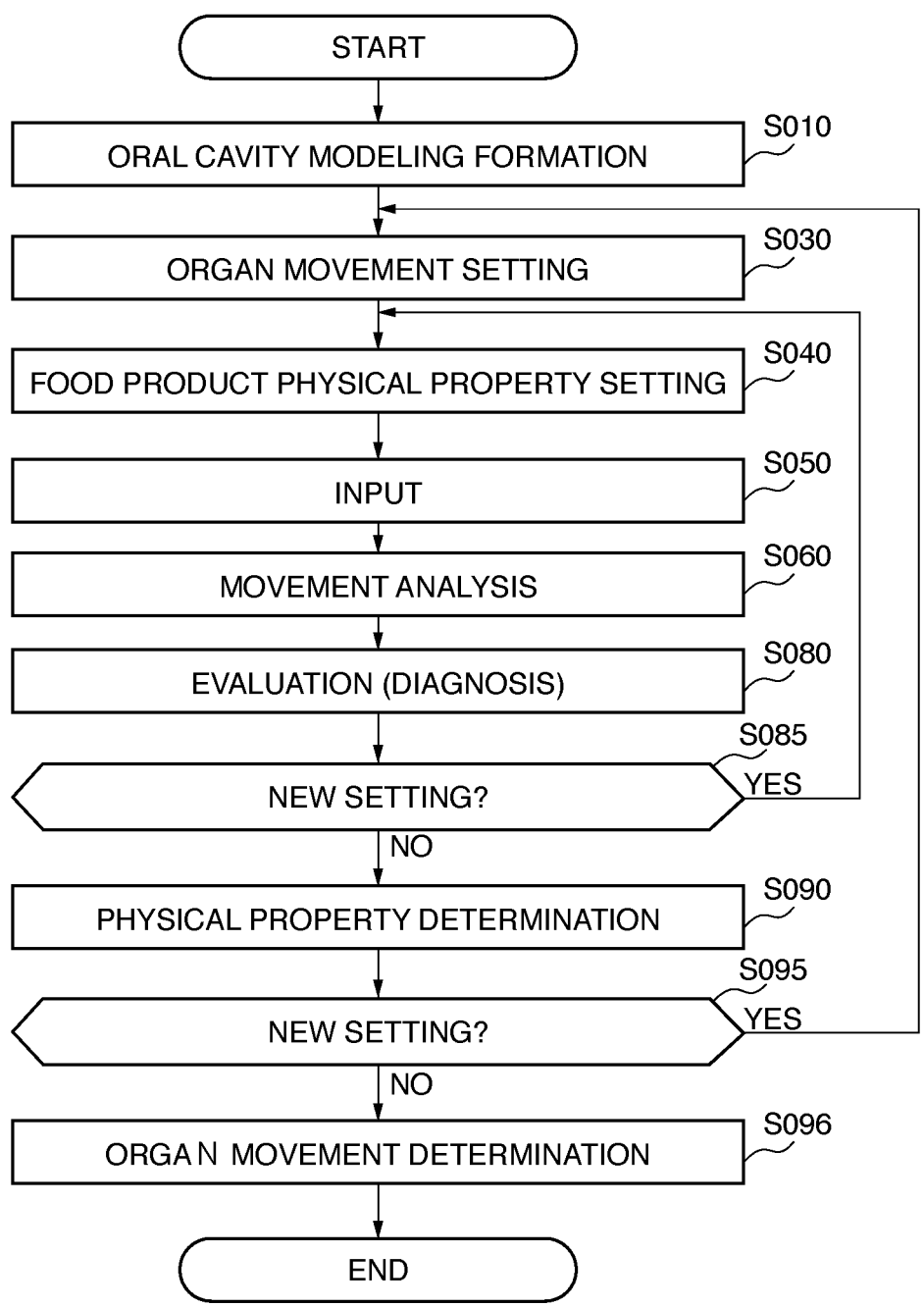
FIG. 16 illustrates an exemplary processing flow of a diagnosis assistance according to the fifth embodiment.

FIG. 16 illustrates an exemplary processing flow of the simulation method according to the embodiment. A loop that changes the organ movement parameter is added to the swallowing simulation method according to the first embodiment (see FIG. 10). That is, after the loop process where the parameter of the physical property is changed, a loop process that changes the organ movement parameter is performed. Here, the physical property determination and the organ properties determination do not find a physical property and an organ movement appropriate for swallowing, but are used as loops that look for the organ movement parameter fitting to the symptom of the patient or the person to be diagnosed for checkup. The processing flows are terminated after simulations are performed with sequentially changed parameters and the physical property and the organ properties fitting to the behavior or the symptom of each oral cavity organ of the patient or the person to be diagnosed for checkup are found (organ movement determination step S096). It is also possible to predict the parameter after the treatment, continue the simulation, and obtain an improvement effect of treatment.

(Program)

The present invention is also applicable as a program readable by the computer to make the computer execute the above described swallowing simulation methods. Additionally, the present invention can be achieved as a storage medium to store the program. The program may be stored to the controller of the swallowing simulation apparatus for use, may be stored to the built-in or external storage device for use, or may be downloaded from the Internet for use.

The preferred embodiments of the present invention are described above. However, the present invention should not be limited to these embodiments. Various improvements are possible without departing from the spirit and the scope of the present invention.

While in the above described embodiments, for example, exemplary movements of the moving wall of the tongue, the soft palate, the epiglottis, and the gullet wall are described, the motion equation and the parameter can be freely changed. Additionally, a movement can be given to other than the above described four organs, for example, a tooth. Thus, an influence of mastication to the swallowing can be reflected. The exemplary food products are up to two. However, the three or more food products can be operated together and the behavior can be analyzed. Further, an analysis of solids with mutually different physical property value, for example, chocolate covering peanuts (solid-solid), an analysis of chocolate incorporating liqueur (solid-liquid), and also an analysis of mixed liquid of liquid (liquid-liquid) with mutually different physical property value, for example, dressing (oil and vinegar) are possible. Besides, the details can be variously changed, for example, the organs and the food products can be displayed in different colors.

INDUSTRIAL APPLICABILITY

The present invention is used for an analysis of a swallowing condition of a food and drink.

Use of the terms "a," "an," "the" and similar referents used in the context in explanation of the invention (particularly in the context of claims as described below) is to be construed to cover both the singular form and the plural form, unless otherwise indicated herein or clearly contradicted by context. The terms "comprising," "having," "including" and "containing" are to be construed as open-ended terms (more specifically, meaning "including, but not limited to") unless otherwise noted. Recitation of ranges of values herein are merely intended to serve as a shorthand method of referring individually to each separate value falling within the range, unless otherwise indicated herein, and each separate value is incorporated herein as if it were individually recited herein. All methods described herein can be performed in any suitable order unless otherwise indicated herein or otherwise clearly contradicted by context. The use of any and all examples, or exemplary language ("such as") provided herein, is intended merely to better illuminate the invention and does not pose a limitation on the scope of the invention unless otherwise claimed. No language herein should be construed as indicating any non-claimed element as essential to the practice of the invention.

Preferred embodiments of the invention are described herein, including the best mode known to the present inventors for carrying out the present invention. Variations of the preferred embodiments may become apparent to those skilled in the art upon reading the foregoing description. The present inventors expect skilled artisans to employ such variations as appropriate, and the present inventors intend for the invention to be practiced otherwise than as specifically described herein. Accordingly, the invention includes all modifications and equivalents of the subject matter recited in the claims appended hereto as permitted by applicable law. Moreover, any combination of the elements in all possible variations thereof is encompassed by the invention unless otherwise indicated herein or otherwise clearly contradicted by context.

DESCRIPTION OF REFERENCE NUMERALS AND SYMBOLS

10 oral cavity modeling unit
11 oral cavity model
12 oral cavity wall
13 gullet
14 respiratory tract
15 tongue
16 soft palate
17 epiglottis
18 moving wall
19 gullet wall
20 organ property setting unit
30 organ movement setting unit
40 food product physical property setting unit
41 to 44, 49 pseudo food product
45 food product input setting unit
50 movement analysis unit
60 evaluation unit 70 physical property determiner
75 organ movement determiner
81 input unit
82 display unit
82A pseudo screen display unit
83 storage unit
83A evaluation condition storage unit
83B evaluation result recording unit
83E determination organ movement condition recording unit
90 controller
100A, 100B, 100C swallowing simulation apparatus
PC personal computer
$t_{nd}$ dimensionless swallowing period

The invention claimed is:

1. A swallowing simulation apparatus, comprising;
an input unit;
a display unit;
an evaluation result recording unit;
a storage unit; and
a computer storing, in a non-transitory computer readable medium, a swallowing simulator software including instructions which, when executed by the computer, the computer controls an oral cavity modeling unit, an organ property setting unit, an organ movement setting unit, a food product physical property setting unit, a movement analysis unit, and a physical property determiner, the computer controlling:
the oral cavity modeling unit to form an oral cavity model formed of oral-cavity organs;
the organ property setting unit to set an organ property of each of the oral-cavity organs in the oral cavity model;
the organ movement setting unit to set a movement of each of the oral-cavity organs in the oral cavity model;
the food product physical property setting unit to set a food product, a medicinal product, or a nonmedicinal product (hereinafter referred to as a food product or similar product) as an analysis target, and a physical property of the food product or similar product;
the input unit to input a pseudo-food product to the oral cavity, the pseudo-food product being formed by modeling the food product or similar product;
the movement analysis unit to analyze a movement of each of the oral-cavity organs and a behavior of the pseudo-food product while being swallowed in the oral-cavity model using a particle method; and
the display unit to display an analysis result of the movement of each of the oral-cavity organs and the behavior of the pseudo-food product while being swallowed on a moving screen, the analysis result being analyzed by the movement analysis unit;
wherein, under control of the computer:
the organ property setting unit sets an oral cavity wall as a rigid body and a tongue as an elastic body;
the organ movement setting unit sets a plurality of moving walls embedded in the tongue, the tongue being set so as to move in a peristaltic movement or a wave movement by moving the plurality of moving walls to a direction intersecting with a surface of the tongue with a predetermined period and a predetermined phase difference, and sets a soft palate, an epiglottis, and a gullet wall so as to move together with a predetermined phase difference to the peristaltic movement or the wave movement;
the movement analysis unit treats the tongue and the pseudo-food product as particles;
the oral cavity modeling unit forms a two dimensional oral cavity model; and
the movement analysis unit analyzes the behavior of the pseudo-food product in a two dimensional space;
the evaluation result recording unit records an evaluation result of easiness of eating and/or easiness of drinking of the food product or similar product based on an analysis result of the behavior of the pseudo-food product while being swallowed;
the physical property determiner determines the physical property of the food product or similar product regarded as appropriate based on the evaluation result recorded in the evaluation result recording unit; and
the storage unit stores, in a non-transitory computer readable medium, the oral cavity model, the organ properties, the analysis result, and the evaluation results,
wherein the evaluation result includes whether the accidental swallowing or accidental ingestion risk exists or not,
wherein the swallowing simulator software includes a two-dimensional particle method analysis software that changes dimensionless physical quantities of the physical property value of the fluid and time,
wherein in the oral cavity model, four portions exclusively are set as the movable parts, the four portions being the tongue, the soft palate, the epiglottis, and an entrance of the gullet,
wherein the movement of three or four of the moving walls embedded in the tongue is performed by changing an amplitude of oscillation of the three or four walls at the same period and shifting a phase.

2. The swallowing simulation apparatus according to claim 1; wherein
the organ movement setting unit sets a movement of the soft palate and the epiglottis as a movement of a rotator where a rotational center moves.

3. The swallowing simulation apparatus according to claim 1; wherein
the food product physical property setting unit sets a plurality of liquid, semisolid, or solid pseudo-food products with different physical property as an analysis target; and
the movement analysis unit determines free surfaces of a plurality of the pseudo-food products and boundaries between the plurality of pseudo-food products, the movement analysis unit analyzing a gearing behavior of the plurality of pseudo-food products.

4. The swallowing simulation apparatus according to claim 1, further comprising;
an evaluation unit configured to evaluate easiness of eating and/or easiness of drinking of the food product or similar product based on the behavior of the pseudo-food product while being swallowed on the moving screen; wherein
the moving screen is a virtual moving screen formed at a virtual space by the swallowing simulation apparatus to simulatively display an analysis result of a movement of each of the oral-cavity organs and a behavior of the pseudo-food product while being swallowed, the analysis result being analyzed by the movement analysis unit; and the evaluation unit evaluates whether the behavior of the pseudo-food product on the virtual moving screen meets a predetermined condition or not.

5. A swallowing simulation method using the swallowing simulation apparatus according to claim 1, the method comprising;
an oral cavity modeling step of forming an oral cavity model formed of oral-cavity organs by the oral cavity modeling unit of the swallowing simulation apparatus;
an organ property setting step of setting an organ property of each of the oral-cavity organs in the oral cavity model by the organ property setting unit of the swallowing simulation apparatus;
an organ movement setting step of setting a movement of each of the oral-cavity organs in the oral cavity model by the oral movement setting unit of the swallowing simulation apparatus;
a food product physical property setting step of setting a food product or similar product as an analysis target and a physical property of the food product or similar product by the food product physical property setting unit of the swallowing simulation apparatus;
an input step of inputting, through the input unit of the swallowing simulation apparatus, a pseudo-food product to the oral cavity, the pseudo-food product being formed by modeling the food product or similar product;
a movement analysis step of analyzing a movement of each of the oral-cavity organs and a behavior of the pseudo-food product while being swallowed in the oral cavity model using a particle method by the movement analysis unit of the swallowing simulation apparatus; and
a display step of displaying an analysis result of the movement of each of the oral-cavity organs and the behavior of the pseudo-food product while being swallowed on a moving screen, the analysis result being analyzed in the movement analysis step by the movement analysis unit of the swallowing simulation apparatus;
wherein:
the organ property setting step sets an oral cavity wall as a rigid body and a tongue as an elastic body;
the organ movement setting step sets a plurality of moving walls in the tongue, the tongue being set so as to move in a peristaltic movement or a wave movement by moving the plurality of moving walls to a direction intersecting with a surface of the tongue with a predetermined period and a predetermined phase difference, and sets a soft palate, an epiglottis, and a gullet wall so as to move together with a predetermined phase difference to the peristaltic movement or the wave movement;
the movement analysis step treats the tongue and the pseudo-food product as particles;
the oral cavity modeling step forms a two dimensional oral cavity model; and
the movement analysis step analyzes the behavior of the pseudo-food product in a two dimensional space;
wherein the swallowing simulation method further comprises:
an evaluation step of evaluating easiness of eating and/or easiness of drinking of the food product or similar product based on an analysis result of the behavior of the pseudo-food product while being swallowed;
an evaluation result recording step configured to record an evaluation result of easiness of eating and/or easiness of drinking of the food product or similar product based on an analysis result of the behavior of the pseudo-food product while being swallowed; and
a physical property determination step of determining a physical property of the food product or similar product regarded as appropriate based on an evaluation result evaluated in the evaluation step, wherein
the evaluation result includes whether the accidental swallowing or accidental ingestion risk exists or not.

6. The swallowing simulation method according to claim 5; wherein
an evaluator makes evaluations observing the moving screen on the display unit and inputs the evaluation results from the input unit.

7. The swallowing simulation apparatus according to claim 1; wherein
an evaluator makes evaluations observing the moving screen on the display unit and inputs the evaluation results from the input unit.

8. A swallowing simulation apparatus, comprising;
an input unit;
an organ movement determiner;
a display unit;
an evaluation result recording unit;
a storage unit; and
a computer storing, in a non-transitory computer readable medium, a swallowing simulator software including instructions which, when executed by the computer, the computer controls an oral cavity modeling unit, an organ property setting unit, an organ movement setting unit, a food product physical property setting unit, a movement analysis unit, and a physical property determiner, the computer controlling:
the oral cavity modeling unit to form an oral cavity model formed of oral-cavity organs;
the organ movement setting unit to set a movement of each of the oral-cavity organs in the oral cavity model;
the food product physical property setting unit to set a food product or similar product as an analysis target and a physical property of the food product or similar product;
the input unit to input a pseudo-food product to the oral cavity, the pseudo-food product being formed by modeling the food product or similar product;
the movement analysis unit to analyze a movement of each of the oral-cavity organs and a behavior of the pseudo-food product while being swallowed in the oral cavity model using a particle method;
the display unit to display an analysis result of the movement of each of the oral cavity organs and the behavior of the pseudo-food product while being swallowed on a moving screen, the analysis result being analyzed by the movement analysis unit; and
the organ movement determiner to determine an organ movement parameter fitting to a behavior or a symptom of an organ of diagnosed person based on the analysis result analyzed in the movement analysis unit in the organ movement parameters set in the organ movement setting unit;
wherein, under control of the computer:
the organ property setting unit sets an oral cavity wall as a rigid body and a tongue as an elastic body;
the organ movement setting unit sets a plurality of moving walls embedded in the tongue, the tongue being set so as to move in a peristaltic movement or a wave movement by moving the plurality of moving walls to a direction intersecting with a surface of the tongue with a predetermined period and a predetermined phase difference, and sets a soft palate, an epiglottis, and a gullet wall so as to move together with a predetermined phase difference to the peristaltic movement or the wave movement;

the movement analysis unit treats the tongue and the pseudo-food product as particles;

the oral cavity modeling unit forms a two dimensional oral cavity model; and the movement analysis unit analyzes the behavior of the pseudo-food product in a two dimensional space;

the evaluation result recording unit to record an evaluation result of easiness of eating and/or easiness of drinking of the food product or similar product based on an analysis result of the behavior of the pseudo-food product while being swallowed;

the storage unit stores, in a non-transitory computer readable medium, the oral cavity model, the organ properties, the analysis result, and the evaluation results, wherein the evaluation result includes whether the accidental swallowing or accidental ingestion risk exists or not, wherein the swallowing simulator software includes a two-dimensional particle method analysis software that changes dimensionless physical quantities of the physical property value of the fluid and time, wherein in the oral cavity model, four portions exclusively are set as the movable parts, the four portions being the tongue, the soft palate, the epiglottis, and an entrance of the gullet, wherein the movement of three or four of the moving walls embedded in the tongue is performed by changing an amplitude of oscillation of the three or four walls at the same period and shifting a phase.

9. A diagnosis assistance apparatus, comprising;

the swallowing simulation apparatus according to claim 8, the swallowing simulation apparatus including the evaluation result recording unit configured to record an evaluation result of easiness of eating and/or easiness of drinking of the food product or similar product based on an analysis result of a behavior of the pseudo-food product while being swallowed;

a medical treatment diagnosis result database that records a diagnosis result on a patient or a person subject to checkup; and a diagnosis result comparator configured to compare a diagnosis result recorded in the medical treatment diagnosis result database with an evaluation result recorded in the evaluation result recording unit.

10. A swallowing simulation method using the swallowing simulation apparatus according to claim 8, the method comprising;

an oral cavity modeling step of forming an oral cavity model formed of oral-cavity organs by the oral cavity modeling unit of the swallowing simulation apparatus;

an organ movement setting step of setting a movement of each of the oral-cavity organs in the oral cavity model by the organ movement setting unit of the swallowing simulation apparatus;

a food product physical property setting step of setting a food product or similar product as an analysis target and a physical property of the food product or similar product by the food product physical property setting unit of the swallowing simulation apparatus;

an input step of inputting, through the input unit of the swallowing simulation apparatus, pseudo-food product to the oral cavity, the pseudo-food product being formed by modeling the food product or similar product;

a movement analysis step of analyzing a movement of each of the oral-cavity organs and a behavior of the pseudo-food product while being swallowed in the oral cavity model using a particle method by the movement analysis unit of the swallowing simulation apparatus;

a display step of displaying an analysis result of the movement of each of the oral-cavity organs and the behavior of the pseudo-food product while being swallowed on a moving screen, the analysis result being analyzed in the movement analysis step by the movement analysis unit of the swallowing simulation apparatus; and an organ movement determination step of determining an organ movement parameter fitting a behavior or a symptom of an organ of diagnosed person based on the analysis result analyzed in the movement analysis step in the organ movement parameters set in the organ movement setting step;

wherein:

the organ property setting step sets an oral cavity wall as a rigid body and a tongue as an elastic body;

the organ movement setting step sets a plurality of moving walls in the tongue, the tongue being set so as to move in a peristaltic movement or a wave movement by moving the plurality of moving walls to a direction intersecting with a surface of the tongue with a predetermined period and a predetermined phase difference, and sets a soft palate, an epiglottis, and a gullet wall so as to move together with a predetermined phase difference to the peristaltic movement or the wave movement;

the movement analysis step treats the tongue and the pseudo-food product as particles;

the oral cavity modeling step forms a two dimensional oral cavity model; and the movement analysis step analyzes the behavior of the pseudo-food product in a two dimensional space;

wherein the swallowing simulation method further comprises:

an evaluation result recording step configured to record an evaluation result of easiness of eating and/or easiness of drinking of the food product or similar product based on an analysis result of the behavior of the pseudo-food product while being swallowed, wherein the evaluation result includes whether the accidental swallowing or accidental ingestion risk exists or not.

11. The swallowing simulation method according to claim 10; wherein an evaluator makes evaluations observing the moving screen on the display unit and inputs the evaluation results from the input unit.

12. The swallowing simulation apparatus according to claim 8; wherein an evaluator makes evaluations observing the moving screen on the display unit and inputs the evaluation results from the input unit.

* * * * *